United States Patent [19]

Pearson et al.

[11] 4,444,771
[45] Apr. 24, 1984

[54] AZETO TRIAZOLO PYRAZINE β-LACTAM ANTIBACTERIAL AGENTS

[75] Inventors: Michael J. Pearson; Clive L. Branch, both of Horsham, England

[73] Assignee: Beecham Group Limited, England

[21] Appl. No.: 299,629

[22] Filed: Sep. 4, 1981

[30] Foreign Application Priority Data

Sep. 13, 1980 [GB] United Kingdom ............... 8029660

[51] Int. Cl.³ .................. C07D 487/14; C07D 205/08; C07D 403/06; A61K 31/495
[52] U.S. Cl. ............................... 424/250; 260/239 A; 260/245.4; 260/330.9; 424/114; 549/214; 544/346
[58] Field of Search .................. 544/346; 424/250

[56] References Cited

U.S. PATENT DOCUMENTS

| | | | |
|---|---|---|---|
| 3,926,955 | 12/1975 | Burton et al. | 424/271 |
| 4,229,443 | 10/1980 | Binderup | 424/200 |
| 4,231,928 | 11/1980 | Naito et al. | 424/251 |
| 4,237,051 | 12/1980 | McCombie | 260/245.2 R |
| 4,244,965 | 1/1981 | Howarth et al. | 424/272 |
| 4,246,262 | 1/1981 | Vangedal | 424/244 |
| 4,252,722 | 2/1981 | Melillo et al. | 424/274 |
| 4,278,686 | 7/1981 | Corbett et al. | 424/272 |

OTHER PUBLICATIONS

Pearson et al., Chem. Abs. 92, 111048 r (1979).

Primary Examiner—Mark L. Berch
Attorney, Agent, or Firm—Jacobs & Jacobs

[57] ABSTRACT

A compound of formula (I) or a salt thereof:

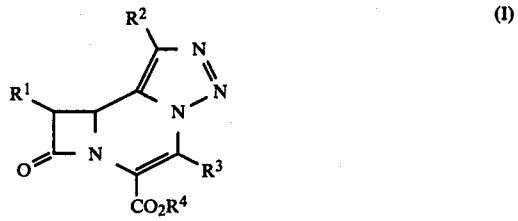

wherein $R^1$ is an amino group, an azido group, or an acylamino group as found in antibacterially active penicillins or cephalosporins;

$R^2$ is a hydrogen atom or a $C_{1-4}$ alkyl group;

$R^3$ is a hydrogen atom, or a $C_{1-4}$ alkyl group optionally substituted by a carboxyl, carboxylic ester, hydroxy, $C_{1-4}$ alkyloxy, acyloxy or heterocyclylthio group; and $R^4$ is hydrogen or a readily removable carboxyl protecting group.

The compounds wherein $R^1$ is an acylamino group are found in known antibacterially active penicillins and cephalosporins and wherein $R^4$ is a hydrogen, a pharmaceutically acceptable salting ion or an in vivo hydrolyzable ester forming radical may be formulated in pharmaceutical compositions.

Processes for the preparation of the compound (I) are also described.

21 Claims, No Drawings

AZETO TRIAZOLO PYRAZINE β-LACTAM ANTIBACTERIAL AGENTS

This invention relates to a class of novel tricyclic β-lactam derivatives, certain of which have antibacterial activity and are of value in the treatment of infections in animals, including man and poultry, caused by a wide range of organisms. In particular the invention relates to a class of fused ring heterocyclic compounds containing the triazole ring structure.

The invention also relates to a process for the preparation of such compounds, intermediates for use in the preparation of the compounds and to pharmaceutical compositions comprising the antibacterially active compounds.

European Patent Application No. 0004134 discloses a class of compounds of the formula (A):

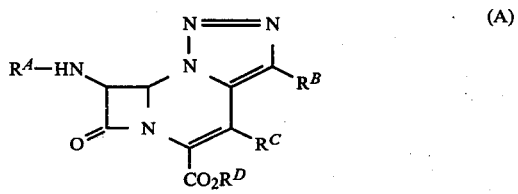

wherein $R^A$ is a hydrogen atom, a trityl group or an acyl group as found in known antibacterially active penicillins or cephalosporins; $R^B$ is a hydrogen atom, a lower alkyl group or an aryl group; $R^C$ is a hydrogen atom, a lower alkyl group, a substituted lower alkyl or a thiosubstituted lower alkyl group; and $R^4$ is a group such that $CO_2R^D$ is a carboxylic acid group or a salt or readily removable ester thereof.

We have now found a class of compounds containing the 6-oxo-azeto-[2,1-c]-v-triazolo-[1,5-a]-pyrazine nucleus, certain of which have antibacterial activity.

According to the present invention there is provided a compound of formula (I) or a salt thereof:

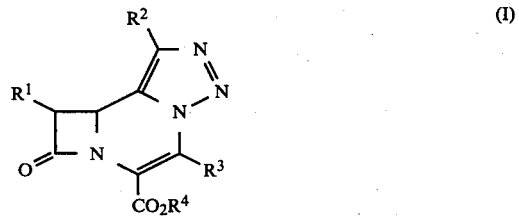

wherein
$R^1$ is an amino group, an azido group, or an acylamino group as found in antibacterially active penicillins or cephalosporins;
$R^2$ is a hydrogen atom or a $C_{1-4}$ alkyl group;
$R^3$ is a hydrogen atom, or a $C_{1-4}$ alkyl group optionally substituted by a carboxy, carboxylic ester, hydroxy, $C_{1-4}$alkyloxy, acyloxy or heterocyclylthio group; and
$R^4$ is hydrogen or a readily removable carboxyl protecting group.

Those compounds of the formula (I) wherein $R^1$ is an amino group, or an azido group are intended mainly as intermediates in the preparation of compounds of the formula (I) wherein $R^1$ is an acylamino group as formed in antibacterially active penicillins or cephalosporins.

Those compounds of the formula (I) wherein $R^4$ is a readily removable carboxyl protecting group or a non-pharmaceutically acceptable salt are intended mainly as intermediates in the preparation of compounds of the formula (I) wherein $R^4$ is a free carboxyl group or a pharmaceutically acceptable salt thereof. Also included within the readily removable carboxyl protecting groups $R^4$ are pharmaceutically acceptable in vivo hydrolysable ester groups.

Examples of suitable pharmaceutically acceptable in vivo hydrolysable ester groups include those which break down readily in the human body to leave the parent acid or its salt, for example acyloxyalkyl groups such as acetoxymethyl, pivaloyloxymethyl, α-acetoxyethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

Suitable values for $R^2$ in the compounds of the formula (I) include the hydrogen atom and methyl, ethyl, propyl and butyl group. Favoured values for $R^2$ include the hydrogen atom and the methyl and ethyl groups. The preferred value for $R^2$ is the hydrogen atom.

Suitable values for $R^3$ in the compounds of the formula (I) include the hydrogen atom and methyl, ethyl, propyl, butyl, acetoxymethyl and heterocyclicthio methyl group.

The heterocyclicthio group may suitably be represented by the formula:

wherein "Het" is a five or six-membered heterocyclic ring containing from 1 to 4 atoms selected from N, O, and S unsubstituted or substituted with one or two groups selected from $C_{1-6}$ alkyl, $C_1$–$C_6$ alkoxy, hydroxyalkyl, $C_1$–$C_6$ alkenyl, alkoxyalkyl, carboxyalkyl, sulphonylalkyl, carbamoyl, carbamoylmethyl, trifluoromethyl, hydroxy, and halogen.

Examples of the group "Het" include unsubstituted and substituted diazolyl, triazolyl, tetrazolyl, thiazolyl, thiadiazolyl, thiatriazolyl, oxazolyl, and oxadiazolyl groups.

Suitable groups "Het" include unsubstituted and substituted 1,2,3-triazolyl; 1,2,4-triazolyl; 1,2,3,4-tetrazolyl; oxazolyl; thiazolyl; 1,3,4-oxadiazolyl; 1,3,4-thiadiazolyl, or 1,2,4-thiadiazolyl. Preferably the heterocyclicthio group is 1-methyl-(1H)-tetrazolylthio, 2-methyl-1,3,4-oxadiazol-5-ylthio, 1-carboxymethyl-(1H)-tetrazolylthio.

From the foregoing it will be realised that the antibacterially active compounds of this invention can be represented by the formula (II) or a pharmaceutically acceptable salt or in vivo hydrolysable ester thereof:

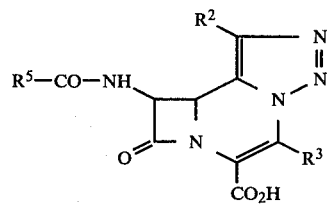

wherein $R^2$ and $R^3$ are as defined with respect to formula (I); and $R^5$ is a group such that $R^5$—CO—NH— is an acylamino group as found in antibacterially active penicillins or cephalosporins.

Suitable groups $R^5CO$ for inclusion in the compounds of the formula (II) include those of the sub-formulae (a)-(d):

$$A_1-(CH_2)_n-\underset{X}{CH}-(CH_2)_m-CO \quad (a)$$

$$A_2-CO \quad (b)$$

$$\begin{array}{c} CH_2 \\ X_1 \\ CH_2 \end{array} C \begin{array}{c} CO \\ X \end{array} \quad (c)$$

$$A_2-X_2-(CH_2)_n-CO \quad (d)$$

wherein n is 0, 1 or 2; m is 0, 1 or 2; $A_1$ is $C_1$-$C_6$ alkyl, $C_3$-$C_6$ cycloalkyl, cyclohexenyl, cyclohexadienyl, phenyl, hydroxy-phenyl, thienyl or pyridyl group; X is a hydrogen or halogen atom, a carboxylic acid, carboxylic ester, azido, tetrazolyl, hydroxy, acyloxy, amino, ureido, guanidino or acylureido group; $A_2$ is an aromatic group such as a phenyl, a 2,6-dimethoxyphenyl, 2-alkoxy-1-naphthyl, 3-arylisoxazolyl or 3-aryl-5-methylisoxazolyl group; $X_1$ is a $CH_2OCH_2$, $CH_2SCH_2$ or $(CH_2)_n$ group; $X_2$ is an oxygen or sulphur atom.

Favoured groups $R^5$ for inclusion in the compounds of the formula (II) include those of the sub-formula (e) and (f):

$$R^6-\underset{R^7}{CH}- \quad (e)$$

$$R^8-\underset{R^9}{CH}- \quad (f)$$

wherein $R^6$ is a phenyl, thienyl or phenoxy group; $R^7$ is a hydrogen atom or methyl group; $R^8$ is a phenyl, p-hydroxyphenyl, thienyl or cyclohexadienyl group; and $R^9$ is a hydroxyl, amino or carboxylic acid group or lower alkyl or phenyl, tolyl or indanyl ester thereof.

One apt group of the sub-formula (e) is the phenoxymethyl group. A second apt group of the sub-formula (e) is the benzyl group. A third apt group of the sub-formula (e) is the thienylmethyl group.

One suitable group of the formula $R^5CO$ is the D-phenylglycyl group.

Another suitable group of the formula $R^5CO$ is the D-p-hydroxyphenylglycyl group.

Another suitable group of the formula $R^5CO$ is the D-mandelyl group.

Another suitable group of the formula $R^5CO$ is the malonyl group.

Another suitable group of the formula $R^5CO$ is the benzoyl group.

Another suitable group of the formula $R^5CO$ is the 2-thienylacetyl group.

Another suitable group of the formula $R^5CO$ is the 3-thienylacetyl group.

Another suitable group of the formula $R^5CO$ is the 2-thienyl-α-carboxyacetyl group.

Another suitable group of the formula $R^5CO$ is the 3-thienyl-α-carboxyacetyl group.

Another suitable group of the formula $R^5CO$ is the phenoxyacetyl group.

Suitable pharmaceutically acceptable salts of the compounds of formula (II) include metal salts e.g. aluminium, alkali metal salts such as sodium or potassium alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins or cephalosporins.

Suitable pharmaceutically acceptable in vivo hydrolysable esters for the compounds of formula (II) include those suitable for compounds within formula (I).

The compounds of this invention which contain a basic group in the acylamino side chain can also form acid addition salts with pharmaceutically acceptable acids such as hydrochloric, or other strong acids. Most suitably those compounds which contain a basic group in the acylamino side chain are in zwitterionic form.

One group of novel intermediates of this invention is that of formula (III):

wherein $R^2$ and $R^3$ are as defined with respect to formula (I) and $R^{10}$ is a readily removable carboxyl blocking group.

Suitable carboxyl-blocking groups $R^{10}$ include ester derivatives of the carboxylic acid. The derivative is one which may readily be cleaved at a later stage in a reaction sequence employing compounds of formula (III).

Since it is advantageous to retain the same carboxyl-protecting group throughout the synthesis, the group $R^{10}$ should preferably also be capable of withstanding the various reagents used in Scheme 1 (see below). We have found benzyl or p-nitrobenzyl esters to be particularly suitable. The free carboxyl group may be regenerated from these by catalytic hydrogenolysis.

A second group of novel intermediates of this invention is that of formula (IV):

wherein $R^2$ and $R^3$ are as defined with respect to formula (I) and $R^{10}$ is as defined with respect to formula (III).

It will be appreciated by those skilled in the art that compounds of structures (I) to (IV) are each capable of existing in four different stereoisomeric forms. From the viewpoint of antibacterial activity the forms having the two hydrogen atoms attached to the β-lactam ring in the cis orientation are preferred to the trans isomers. Moreover, the synthetic optically inactive cis compounds may themselves be separated by general methods known in the art into optically active (+) and (−) components. One method of accomplishing this is illustrated in Examples 5 and 6. The stereoisomer of (II) having the best antibacterial activity is believed to have the absolute stereochemistry shown in (V):

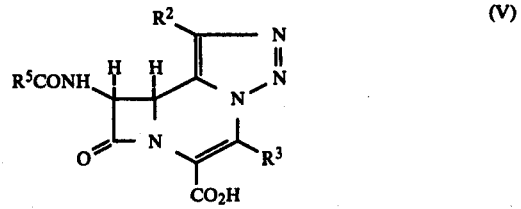

The compounds of the present invention may be prepared according to the general sequence outlined in Scheme 1.

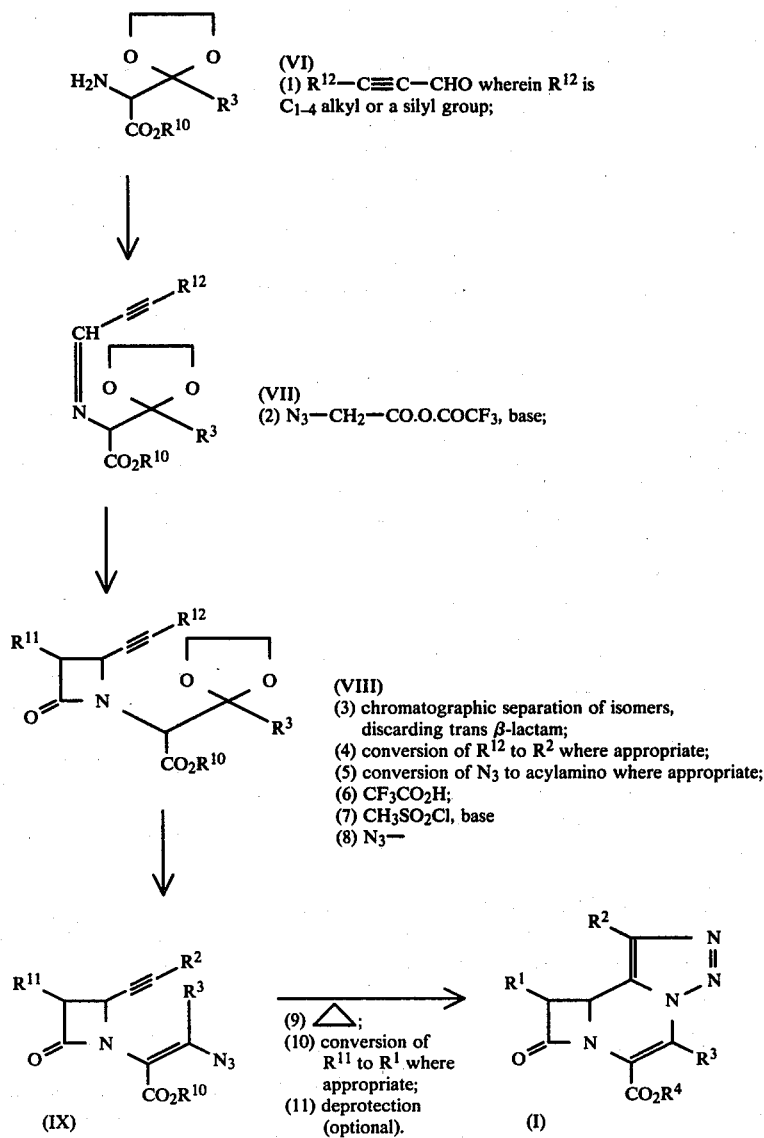

The present invention provides a process for the preparation of the compounds of formula (I) as hereinbefore defined which process comprises the cyclisation of a compound of formula (IX):

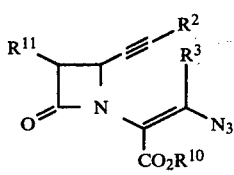 (IX)

wherein $R^2$ and $R^3$ are as described hereinbefore with respect to formula (I) and wherein any reactive groups may be protected; and $R^{10}$ is as defined with respect to formula (III) hereinbefore; $R^{11}$ is azido or acylamino and thereafter where necessary carrying out one or more of the following:

(a) removing any protecting groups on group $R^1$,
(b) removing a carboxyl blocking group $R^{10}$, and
(c) converting the compound to a salt thereof.

The cyclisation is generally carried out in an inert organic solvent or solvent mixture, such as, for example benzene, toluene, diethylether, tetrahydrofuran or ethyl acetate at a moderate temperature i.e. greater than room temperature, the reflux temperature of the solvent being selected for convenience. The period for which the reaction is allowed to proceed depends upon the particular starting materials employed. The course of the reaction may be followed by conventional methods such as thin layer chromatography and terminated when an optimum quantity of product is present in the reaction mixture.

Purification of the compound may be accomplished by conventional recrystallisation or chromatographic techniques.

The preparation and reaction of the intermediates (VI), (VII), (VIII) and (IX) may be carried out by the general methods as described in Scheme 1 and as described in the Examples hereinafter.

A further suitable process for the preparation of the antibacterially active compounds of formula (II) herein comprises reacting the compound of formula (III) or an activated derivative thereof with an N-acylating derivative of a carboxylic acid of formula (X):

$$R^5\text{—}CO_2H \qquad (X)$$

wherein $R^5$ is as defined with respect to formula (II) hereinbefore and in which any reactive groups may be protected and thereafter performing one or more of the following:

(a) removing any protecting groups on the group $R^5$;
(b) reoving the carboxyl blocking group $R^{10}$;
(c) converting the product into a salt or in vivo hydrolysable ester thereof.

Suitable groups which permit acylation to take place and which are optionally present on the amino group of the starting material of the formula (III) include N-silyl, N-stannyl and N-phosphorus groups, for example trialkylsilyl groups such as trimethylsilyl, trialkyltin groups such as tri-n-butyltin, groups of formula —P.$R^aR^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P(OC$_2$H$_5$)$_2$'—P(C$_2$H$_5$)$_2$'

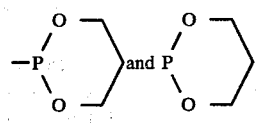

Suitable N-acylating derivatives of carboxylic acid (X) include an acid halide, preferably the acid chloride or bromide. Acylation with an acid halide may be affected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C$_{1-6}$)-1,2-alkylene oxide-such as ethylene oxide or propylene oxide.

The acid halide may be prepared by reacting the acid (X) or a salt thereof with a halogenating (e.g. chlorinating or brominating) agent such as phosphorus pentachloride, thionyl chloride or oxalyl chloride.

Alternatively, the N-acylating derivative of the acid (X) may be symmetrical or mixed anhydride. Suitable mixed anhydrides are alkoxyformic anhydrides.

Alternative N-acylating derivatives of acid (X) are the acid azide, or activated esters such as esters with 2-mercaptopyridine, cyanomethanol, p-nitrophenol, 2,4-dinitrophenol, thiophenol, halophenols, including pentachlorophenol, monomethoxyphenols or 8-hydroxyquinoline; or amides such as N-acylsaccharins or N-acylphthalimides or N-acylsuccinimides.

Other reactive N-acylating derivatives of the acid (X) include the reactive intermediate formed by reaction in situ with a condensing agent such as a carbodiimide, for example N,N-diethyl-, dipropyl- or diisopropylcarbodiimide, or N,N'-di-cyclohexylcarbodiimide. The condensation reaction is preferably carried out in an organic reaction medium, for example methylene chloride, dimethylformamide, acetonitrile, alcohol, benzene, dioxan, or tetrahydrofuran.

The intermediate of formula (IV) herein is in turn a valuable precursor for the intermediate of formula (III) herein. Conversion of the compound of formula (IV) to that of formula (III) may be accomplished by catalytic hydrogenation or chemical reduction.

Suitable hydrogenation catalysts include platinum oxide, palladium on carbon or Raney nickel.

Suitable chemical reducing agents for performing the conversion of the azido group to an amino group include, for example, sodium bisulphite, sodium sulphide, sodium arsenite, titanous chloride, and hydrogen sulphide. Preferably the reducing agent is hydrogen sulphide in the presence of triethylamine.

The antibiotic compounds according to the invention may be formulated for administration in any convenient way for use in human or veterinary medicine, by analogy with other antibiotics, and the invention therefore includes within its scope a pharmaceutical composition comprising a compound of formula (II) above together with a pharmaceutical carrier or excipient.

The compositions may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for oral administration may be in unit does presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almound oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration.

The compound of formula (II) may be the sole therapeutic agent in the compositions of the invention or a combination with other antibiotics may be employed. Advantageously the compositions also comprise a compound of formula (XI) or a pharmaceutically acceptable salt or ester thereof:

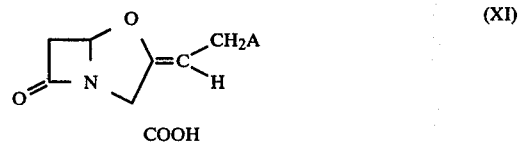

wherein A is hydroxyl, substituted hydroxyl, thiol, substituted thiol, amino, mono- or di-hydrocarbyl-substituted amino, or mono- or di-acylamino.

The following Examples illustrate the preparation of some of the compounds of this invention.

EXAMPLE 1

(4bRS,5RS)5,6-Dihydro-9-methyl-6-oxo-5-phenoxyacetamido-4bH-azeto-[2,1-c]-v-triazolo-[1,5-a]-pyrazine-8-carboxylic acid (15)

(a) Benzyl α-(3-Trimethylsilylpropynylidene amino)acetoacetate ethylene ketal (2)

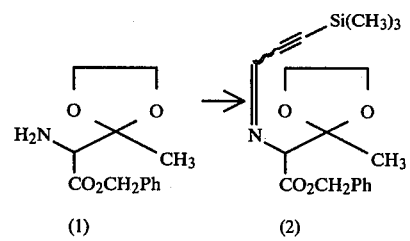

Trimethylsilylprop-2-yn-1-al [prepared from trimethylsilylethynyllithium (L. Brandsma et al., Rec. trav. Chim, 1975, 94 163) and ethyl formate according to the procedure of H. Hauptmann and M. Mader, Synthesis, 1978, 4, 307] (9.0 g) in dry methylene dichloride (250 ml) was vigorously stirred with benzyl α-aminoacetoacetate ethylene ketal (1) (17.93 g) (see T. W. Doyle et al, Canad, J. Chem., 1977, 55, 484) and anhydrous magnesium sulphate (5 g) at ambient temperature for nineteen hours. The mixture was filtered and the filtrate evaporated. The residue was dried in vacuo to give the Schiff base (2) as a pale orange gum (23 g), $\nu_{max}$. (CHCl$_3$) 1738, 1610 cm$^{-1}$.

(b)
(3RS,4RS)-3-Azido-1-(1-benzyloxycarbonyl-2,2-ethyleneketalpropyl)-4-trimethylsilylethynyl-azetidin-2-one (3),
(3RS,4SR)-3-Azido-1-[(1RR)-1-benzyloxycarbonyl-2,2-ethyleneketalpropyl]-4-trimethylsilylethynyl-azetidin-2-one (4) and
(3RS,4SR)-3-Azido-1-[(1SS)-1-benzyloxycarbonyl-2,2-ethyleneketalpropyl]-4-trimethylsilylethynylazetidin-2-one (5)

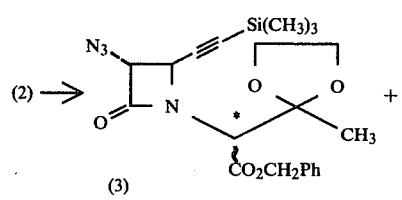

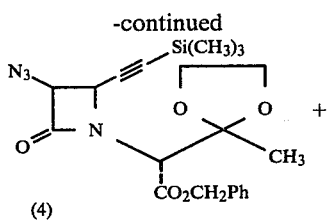

(4)

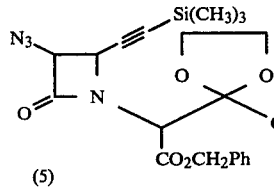

(5)

Azidoacetic acid (9.71 g) was dissolved in dry methylene dichloride (80 ml) at 0° under argon and trifluoroacetic anhydride (13.54 ml) added dropwise over ten minutes. After fifteen minutes, triethylamine (13.48 ml) in methylene dichloride (10 ml) was carefully added dropwise over fifteen minutes and stirring at 0° continued a further forty-five minutes. The solution was transferred under argon to a dropping funnel, cooled to −76°, and added over one hour to a mixture of the Schiff base (2) (23 g) and triethylamine (13.48 ml) in methylene dichloride (200 ml) at 0°. After a further one hour at 0° the solution was diluted with methylene dichloride, washed successively with water, dilute NaHCO$_3$ solution, brine, dired (MgSO$_4$) and evaporated. Chromatography of the residue on silica H gave the trans β-lactam (3) (6.93 g) as a mixture of isomers (*) ( ≃4:1) $v_{max}$. (CHCl$_3$) 2170, 2120, 1780, 1745 cm$^{-1}$; δ ppm (CHCl$_3$) 0.2 (9H, s), 1.43 (0.6H, s), 1.51 (2.4H, s), 3.91 (3.2H, s), 3.93 (0.8H, s,), 4.3 (0.2H, d, J ≃ 2 Hz), 4.36 (0.8H, s), 4.46 (0.8H, d, J ≃ 2 Hz), 4.47 (0.2H, s), 4.53 (1H, d, J ≃ 2 Hz), 5.15 (0.4H, AA'), 5.11 and 5.27 (1.6H, ABq, J 12 Hz), 7.35 (5H, s). (Found: C, 57.0; H, 5.9; N, 12.7; C$_{21}$H$_{26}$N$_4$O$_5$Si requires C, 57.0; H, 5.9; N, 12.7%).

Further elution of the column provided (4) (4.85 g) as an oil. $v_{max}$. (CHCl$_3$) 2120, 1770, 1740 cm$^{-1}$; δ ppm (CDCl$_3$) 0.2 (9H, s), 1.54 (3H, s), 3.88 (4H, s), 4.47 (1H, d, J 5 Hz), 4.52 (1H, s), 4.92 (1H, d, J 5 Hz), 5.09 and 5.24 (2H, ABq, J 12 Hz), 7.53 (5H, s). (Found: C, 57.1; H, 6.1; N, 12.8%), and then (5) (2.23 g), m.p. 70°–72° (ether); $v_{max}$. (Nujol) 2130, 1793, 1740 cm$^{-1}$, δ ppm (CDCl$_3$) 0.18 (9H, s), 1.40 (3H, s), 3.90 (4H, s), 4.49 (1H, d, J 5 Hz), 4.50 (1H, d, J 5 Hz), 5.09 and 5.26 (2H, ABq, J 12 Hz), 7.33 (5H, s). (Found: C, 57.1; H, 6.0; N, 12.6%).

(c)
(3RS,4SR)-3-Azido-1-[(1RR)-1-benzyloxycarbonyl-2,2-ethyleneketalpropyl]-4-ethynyl-azetidin-2-one (6) and
(3RS,4SR)-3-Azido-1-[(1SS)-1-benzyloxycarbonyl-2,2-ethyleneketalpropyl]-4-ethynyl-azetidin-2-one (7)

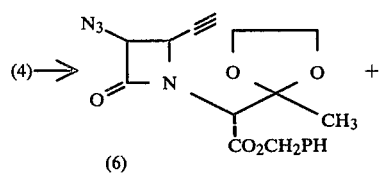

(6)

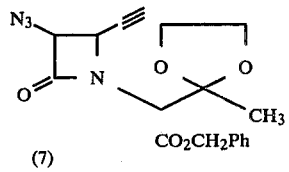

(7)

To the β-lactam (4: 0.411 g) in dry tetrahydrofuran (10 ml) was added tetraethylammonium fluoride (0.140 g) and the mixture vigorously stirred at ambient temperature for twenty minutes. The reaction mixture was poured into ethyl acetate, washed with brine, dried (MgSO$_4$) and evaporated. Chromatography of the residue on silica H afforded the product (6) (0.144 g) as a white crystalline solid, m.p. 89°–91° (ethyl acetate-light petroleum); $v_{max}$. (Nujol) 3250, 2100, 1765, 1630 cm$^{-1}$; δ ppm (CDCl$_3$) 1.49 (3H, s), 2.62 (1H, d, J 2 Hz), 3.87 (4H, s), 4.52 (1H, s), 4.58 (1H, d, J 5 Hz), 4.94 (1H, dd, J 5 and 2 Hz), 5.09 and 5.24 (2H, ABq, J 12 Hz) 7.33 (5H, s). (Found: C, 58.3; H, 4.8; N, 15.0; C$_{18}$H$_{18}$N$_4$O$_5$ requires C, 58.4; H, 4.9; N, 15.1%).

Further elution of the column afforded (7) (0.086 g) as a clear oil. $v_{max}$. (CHCl$_3$) 3300, 2120, 1775, 1745 cm$^{-1}$; δ ppm (CDCl$_3$) 1.41 (3H, 2), 2.47 (1H, d, J 2 Hz), 3.93 (4H, s), 4.56 (1H, s), 4.61 (1H, d, J 6 Hz), 4.74 (1H, dd, J 6 and 2 Hz), 5.18 (2H, s), 7.35 (5H, s). (Found: C, 58.5; H, 5.2; N, 15.1%). Similarly, the β-lactam (5) (0.111 g) afforded (6) (0.040 g) and (7) (0.019 g).

(d)
(3RS,4SR)-1-(1-Benzyloxycarbonyl-2,2-ethyleneketalpropyl)-4-ethynyl-3-phenoxyacetamido-azetidin-2-one
(10)

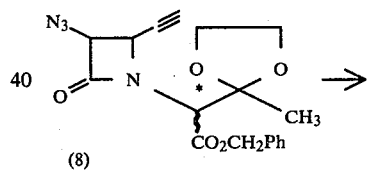

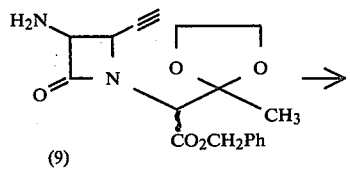

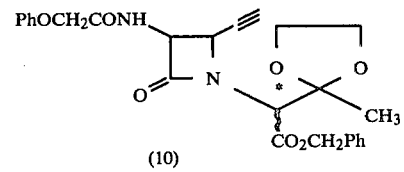

To the β-lactam [8; ca. 2:1 mixture of (6) and (7)] (2 g) in dry methylene chloride (45 ml) at 0° was added triethylamine (0.84 ml). Hydrogen sulphide was bubbled through the mixture of five minutes and the resulting pale yellow solution stood at 0° for twenty-five minutes. The solvent was then removed under reduced pressure and the residue re-evaporated (×3) from methylene dichloride to afford the crude amine (9) as an orange solid. Without further purification, the β-lactam (9) was dissolved in dry methylene dichloride (40 ml) at −20° and triethylamine (0.84 ml) added, followed by dropwise addition of phenoxyacetyl chloride (0.84 ml) in methylene dichloride (3 ml) over ten minutes. The reaction mixture was diluted with methylene dichloride, washed with brine, dried (MgSO₄) and evaporated to a gum. Chromatography on silica H afforded the product (10) (2.27 g) as an inseparable mixture of isomers (*) (2:1). $\nu_{max}$. (CHCl₃) 3420, 3315, 1780, 1750, 1698 cm⁻¹; δ ppm (CDCl₃) (deduced from the mixture). Epimer 1. 1.38 (3H, s), 2.21 (1H, d, J 2 Hz), 3.92 (4H, s), 4.54 (2H, s), 4.62 (1H, s), 4.83 (1H, dd, J 5 and 2 Hz), 5.18 (2H, s), 5.58 (1H, dd, J 10 and 6 Hz), 6.8–7.6 (11H, m). Epimer 2. 1.51 (3H, s), 2.36 (1H, d, J 2 Hz), 3.89 (4H, s), 4.54 (3H, s, —CH₂— of the side-chain obscures the methine proton), 4.98 (1H, d, J 5 and 2 Hz), 5.18 (2H, s), 5.54 (1H, dd, J 10 and 6 Hz), 6.8–7.6 (11H, m). (Found: M⁺, 478.1708; C₂₆H₂₆N₂O₇ requires M, 478,1737).

(e) (3RS,4SR)-1-(1-Benzyloxycarbonyl-2-hydroxyprop-1-enyl)-4-ethynyl-3-phenoxy-acetamido-azetidin-2-one (11)

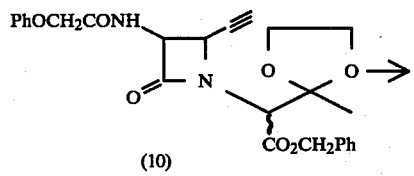

(10)

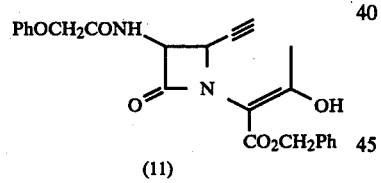

(11)

The ethylene ketal (10; 0.464 g) was dissolved in trifluoroacetic acid (5 ml) and the solution kept at room temperature for one hour. The mixture was then poured into methylene dichloride/ice-water and the organic phase separated. The aqueous layer was reextracted with methylene dichloride and the combined extracts washed with water until neutral, then washed with brine, dried (MgSO₄), and evaporated. Chromatography of the residue on silica H provided the product (11) (0.17 g) as a crystalline solid, m.p. 115°–116° (ethyl acetate-light petroleum); $\nu_{max}$. (Nujol) 3345, 3260, 1780, 1755, 1695, 1660, 1620 cm⁻¹; δ ppm (CDCl₃) 2.16 (3H, s), 2.31 (1H, d, J 2 Hz), 4.56 (2H, s), 4.59 (1H, dd, J 5 and 2 Hz), 5.18 (2H, s), 5.38 (1H, dd, J 9 and 5 Hz, collapses to d, J 5 Hz on exchange), 6.8–7.4 (11H, m), 12.32 (1H, s, exchange). Found: C, 66.2; H, 4.8; N, 6.3; C₂₄H₂₂N₂O₆ requires C, 66.4; H, 5.1; N, 6.5%).

(f) (3RS,4SR)-1-(1-Benzyloxycarbonyl-1-mesyloxyprop-1-enyl)-4-ethynyl-3-phenoxyacetamido-azetidin-2-one (12)

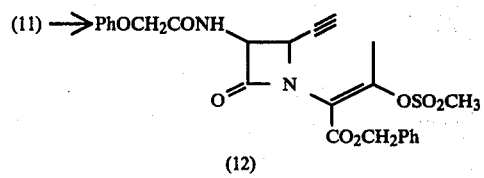

(12)

To the β-lactam (11) (0.217 g) in dry methylene dichloride (8 ml) at 0° was added triethylamine (0.056 g), followed by methanesulphonyl chloride (0.063 g) in a little methylene dichloride (0.5 ml), dropwise over one minute. After twenty minutes the reaction mixture was washed with a little brine, dried (MgSO₄) and evaporated to an oil. Chromatography on silica H gave the mesylate (12) (0.181 g) as an amorphous solid. $\nu_{max}$. (CHCl₃) 3420, 3310, 1785, 1750, 1695, 1645 cm⁻¹; δ ppm (CDCl₃) 2.32 (1H, d, J 2 Hz), 2.57 (3H, s), 3.14 (3H, s), 4.51 (2H, s), 4.83 (1H, dd, J 5 and 2 Hz), 5.2 (2H, s), 5.47 (1H, dd, J 9 and 5 Hz), 6.8–7.5 (11H, m). Inter alia peaks at δ 2.39 and δ 2.99 are assumed to belong to the minor Z-isomer. (Found: M⁺, 512.1253; C₂₅H₂₄N₂O₈S requires M, 512.1251).

(g) (4bRS,5RS) Benzyl 5,6-Dihydro-9-methyl-6-oxo-5-phenoxyacetamido-4bH-azeto[2,1-c]-v-triazolo-[1,5-a]-pyrazine-8-carboxhlate (14)

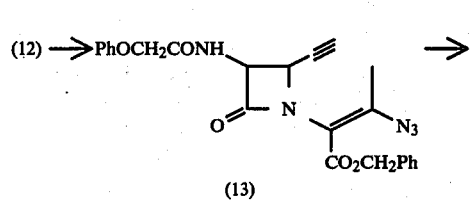

(13)

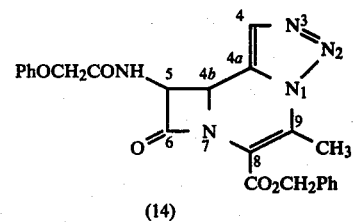

(14)

The mesylate (12) (0.142 g) in dry mimethylformamide (3 ml) was vigorously stirred with finely powdered sodium azide (0.02 g) at room temperature for ten minutes. The reaction mixture was poured into ethyl acetate, washed with water, very dilute HCl, brine, dried (MgSO₄) and evaporated to give (13) as an oil. $\nu_{max}$. (CHCl₃) 3400, 3300, 2120, 1785, 1730, 1695, 1630 cm⁻¹.

The total crude product (13) was kept in benzene (20 ml) at room temperature for seventeen hours and then the solution refluxed for ten minutes, cooled and evaporated to a gum. Chromatography on silica H, followed by ether trituration, provided the product (14) as an amorphous white solid (0.062 g). $\nu_{max}$. (EtOH) 301 nm (ε9500); $\nu_{max}$. (CHCl₃) 3410, 1790, 1720, 1690, 1630 cm⁻¹; δ ppm (CDCl₃) 2.9 (3H, s), 4.48 (2H, s), 5.1 (1H, d, J 5 Hz), 5.3 (2H, s), 5.84 (1H, dd, J 8 and 5 Hz), 6.7-7.5 (12H, m). (Found: C, 62.4; H, 4.4; N, 14.7; C$_{24}$H$_{21}$N$_5$O$_5$ requires C, 62.7; H, 4.6; N, 15.3%). (C.I. Mass spectra showed an M$^+$+H of 460. E.I. showed no M$^+$ but very strong peaks at m/e 268 and 191 resulting from β-lactam cleavage. Found: m/e 268.0964, C$_{14}$H$_{12}$N$_4$O$_2$ requires m/e 268.0960 and m/e 191.0581, C$_{10}$H$_9$NO$_3$ requires m/e 191.0582).

(h) (4bRS,5RS) 5,6-Dihydro-9-methyl-6-oxo-5-phenoxyacetamido-4bH-azeto-[2,1-c]v-triazolo-[1,5-a]-pyrazine-8-carboxylic acid (15)

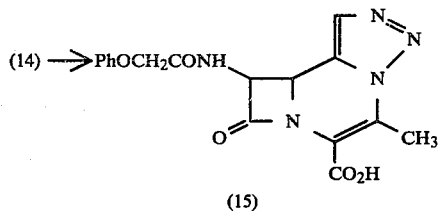

(15)

The ester (14) (40 mg) was dissolved in dioxan (15 ml) and water (3 ml) and hydrogenated using 10% palladium/carbon catalyst (20 mg). The mixture was filtered through Kieselguh, and the filtrate evaporated to dryness, followed by re-evaporation from ethanol, then toluene to give a gum. Trituration with ether provided the acid (15) (30 mg) as a white solid. λ$_{max.}$ (EtOH) 288 n.m. (ε6400); ν$_{max.}$ (KBr) 3400b, 1760, 1675, 1630 cm$^{-1}$; δ ppm (CD$_3$OD/D$_2$O) 2.81 (3H, s), 5.25 (1H, dd, J 5 and ≈ 1 Hz), 5.67 (1H, d, J 5 Hz), 6.5-7.5 (5H, m), 7.6 (1H, d, J ≈ 1 Hz).

EXAMPLE 2

(4bRS,5RS)5,6-Dihydro-9-methyl-6-oxo-[DL-α-phenoxy carbonylphenylacetamido]-4bH-azeto[2,1-c-]-v-triazolo[1,5-a]-pyrazine-8-carboxyl acid (22)

(a) (3RS,4SR)-1-(1-Benzyloxycarbonyl-2,2-ethyleneketal-propyl)-4-ethynyl-3-DL-α-phenoxycarbonyl-phenylacetamidoazetidin-2-one (17)

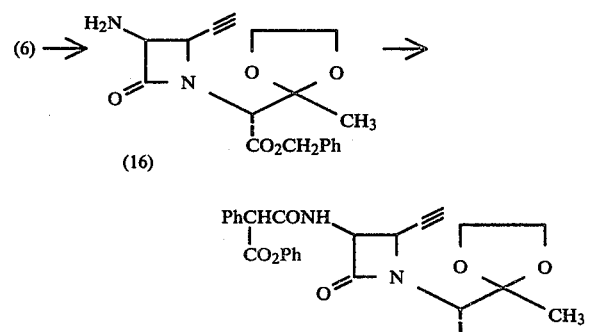

As described in Example 1(d) for the epimeric mixtures (8) and (9), the azide (6) (0.88 g) was reduced to the amine (16) and subsequently reacted with freshly prepared DL-αphenoxycarbonylphenylacetal chloride (1.0 g) to give the acylamino derivative (17) (1.07 g) as a white amorphous solid. ν$_{max.}$ (CHCl$_3$) 3310, 1775, 1745, 1690 cm$^{-1}$; δ ppm (CDCl$_3$) 2.23 (0.5H, d, J 2 Hz), 2.38 (0.5H, d, J 2 Hz), 3.86 (4H, s), 4.49 (0.5H, s), 4.81 (0.5H, s), 4.92 (1H, dd, J 5 and 2 Hz) 5.09 and 5.24 (2H, ABq, J 12 Hz), 5.42 (0.5H, dd, J 9 and 5 Hz), 5.47 (0.5H, dd, J 9 and 5 Hz), 5.8-7.6 (15H, m), 7.65 (1H, d, J 9 Hz exch.). (Found: C, 67.5; H, 5.4; N, 4.6; C$_{33}$H$_{30}$N$_2$O$_8$ requires C, 68.0; H, 5.2; N, 4.8%).

(b) (3RS,4SR)-1-(1-Benzyloxycarbonyl-2-hydroxyprop-1-enyl)-4-ethynyl-3-DL-α-phenoxycarbonyl-phenylacetamidoazetidin-2-one (18)

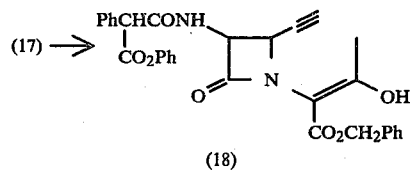

(18)

The ethylene ketal (17; 0.736 g) was dissolved in trifluoroacetic acid (7.36 ml) and water (0.368 ml) and kept at ambient temperature for one hour. The solution was evaporated to dryness and then re-evaporated from toluene (×2), to give an oil). The latter was dissolved in ethyl acetate, washed successively with dilute NaHCO$_3$ solution and brine, dried (MgSO$_4$) and evaporated. Chromatography on silica H afforded the product (18) (0.442 g) as an amorphous white solid. ν$_{max.}$ (CHCl$_3$) 3310, 1775, 1750, 1695, 1660 sh, 1620 cm$^{-1}$; δ ppm (CDCl$_3$) 2.1 (3H, s), 2.16 (0.5H, d, J 2 Hz), 2.34 (0.5H, d, J 2 Hz), 4.54 (1H, dd, J 5 and 2 Hz), 4.8 (1H, s), 5.16 (2H, AA', J 12 Hz), 5.31 (0.5H, dd, J 9 and 5 Hz, collapsing to d, J 5 Hz on exchange), 5.34 (0.5H, dd, J 9 and 5 Hz, collapsing to d, J 5 Hz on exchange), 6.9-7.7 (15H, m), 7.92 (1H, d, J 9 Hz, exchange). (Found: M$^+$ 538.1771; C$_{31}$H$_{26}$N$_2$O$_7$ requires M, 538.1739).

(b) (3RS,4SR)-1-(1-Benzyloxycarbonyl-2-hydroxyprop-1-enyl)-4-ethynyl-3-Dl-α-phenoxycarbonyl-phenylacetamidoazetidin-2-one (18)

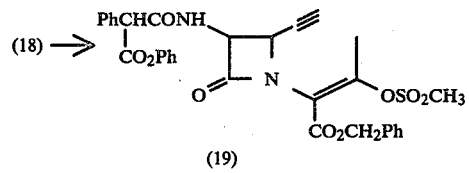

(19)

The ethylene ketal (17; 0.736 g) was dissolved in trifluoroacetic acid (7.36 ml) and water (0.368 ml) and kept at ambient temperature for one hour. The solution was evaporated to dryness and then re-evaporated from toluene (×2), to give an oil. The latter was dissolved in ethyl acetate, washed successively with dilute NaHCO$_3$ solution and brine, dried (MgSO$_4$) and evaporated. Chromatography on silica H afforded the product (18) (0.442 g) as an amorphous white solid. ν$_{max.}$ (CHCl$_3$) 3310, 1775, 1750, 1695, 1660 sh, 1620 cm$^{-1}$; δ ppm (CDCl$_3$) 2.1 (3H, s), 2.16 (0.5H, d, J 2 Hz), 2.34 (0.5H, d, J 2 Hz), 4.54 (1H, d,, J 5 and 2 Hz), 4.8 (1H, s), 5.16 (2H, AA', J 12 Hz), 5.31 (0.5H, dd, J 9 and 5 Hz, collapsing to d, J 5 Hz on exchange), 5.34 (0.5H, dd, J 9 and 5 Hz, collapsing to d, J 5 Hz on exchange), 6.9-7.7 (15H, m), 7.92 (1H, d, J 9 Hz, exchange). (Found: M$^+$ 538.1771; C$_{31}$H$_{26}$N$_2$O$_7$ requires M, 538.1739).

(c)
(3RS,4SR)-1-(1-Benzyloxycarbonyl-2-mesyloxyprop-1-enyl)-4-ethynyl-3-DL-α-phenoxycarbonyl-phenylacetamidoazetidin-2-one (19)

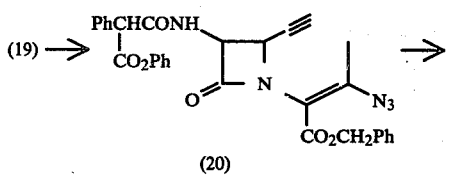

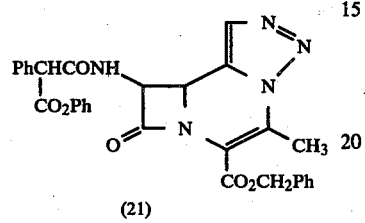

The β-lactam (18; 0.445 g) was transformed into the mesylate (19) (0.474 g) as described in Example 1(f). ν$_{max}$. (CHCl$_3$) 3300, 1780, 1735, 1690, 1640 cm$^{-1}$; δ ppm (CDCl$_3$) 2.19 (0.5H, d, J 2 Hz), 2.34 (0.5H, d, J 2 Hz), 2.56 (3H, s), 3.1 (3H, s), 4.74 (1H, m), 4.78 (1H, s), 5.16 (2H, s), 5.25–5.40 (1H, m), 6.9–7.7 (15H, m), 7.7 (1H, d, J 9 Hz, exchange). Inter alia peaks at δ 2.43 and δ 2.97 are attributable to the minor Z-isomer. (Found: M$^+$, 616.1533; C$_{32}$H$_{28}$N$_2$O$_9$S requires M, 616.1515).

(d) (4bRS,5RS) Benzyl
5,6-Dihydro-9-methyl-6-oxo-5-[DL-α-phenoxycarbonylphenylacetamido]-4bH-azeto-[2,1-c]-v-triazolo[1,5-a]-pyrazine-8-carboxylate (21)

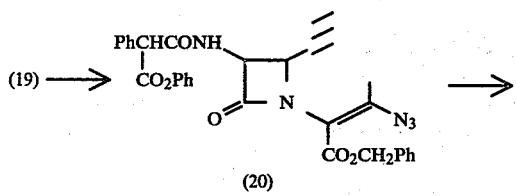

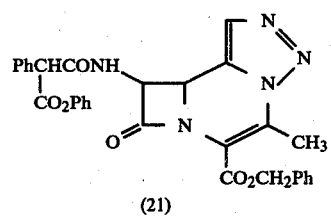

The mesylate (19) (0.3 g) was converted via the vinyl azide (20). ν$_{max}$. (CHCl$_3$) 3310, 2120, 1780, 1730, 1690 cm$^{-1}$ into the lactam (21) (0.074 g) as described in Example 1 (g). λ$_{max}$. (EtOH) 300 nm (ε 7990); ν$_{max}$. (CHCl$_3$) 1790, 1740, 1720, 1685, 1630 cm$^{-1}$; δ ppm (CDCl$_3$) 2.84 (3H, s), 4.76 (two lines together 1H), 5.00 (1H, d, J 5 Hz), 5.27 (2H, s), 5.6–5.8 (1H, m), 6.9–7.7 (16H, m). (Found: M$^+$-OPh, 469.1354; C$_{25}$H$_{19}$N$_5$O$_5$ requires M-OPh, 469.1386).

(e) (4bRS,5RS)
5,6-Dihydro-9-methyl-6-oxo-5-[DL-α-phenoxycarbonylphenylacetamido]-4bH-azeto[2.1-c]-v-triazolo[1.5-a]-pyrazine-8-carboxylic acid (22)

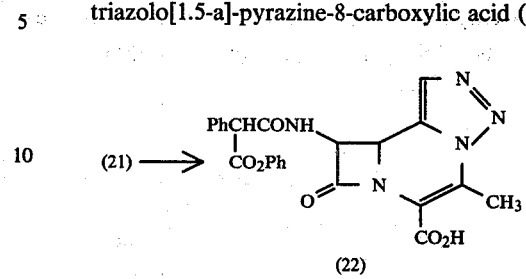

The ester (21) (35 mg) was hydrogenated as described in Example 1(h) to provide the free acid (22) (24 mg) as a white powder. λ$_{max}$. (EtOH) 287 nm (ε 6660); ν$_{max}$. (KBr) 3420b, 1765, 1680, 1630 cm$^{-1}$.

EXAMPLE 3
(4bRS,5RS)-5,6-Dihydro-9-methyl-6-oxo-5-D-α-phenylglyaylamino-4bH-azeto-[2,1-c]-v-triazolo[1,5-a]-pyrazine-8-carboxylic acid, p-toluidine salt (28)

(a)
(3RS,4SR)-1-(1-Benzyloxycarbonyl-2,2-ethyleneketalpropyl)-4-ethynyl-3-(N-[p-nitrobenzyloxycarbonyl]-D-α-phenylglycylamino)-azetidin-2-one (23)

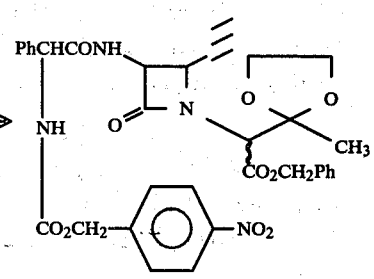

The β-lactam (8) (1.8 g) was reduced to the amine (9) as described in Example 1(d). To methyl chloroformate (0.47 ml) in dry tetrahydrofuran (40 ml), cooled to −10°, was added, dropwise over ten minutes, a solution of N-p-nitrobenzyloxycarbonyl-D-α-phenylglycine (1.82 g), triethylamine (0.777 ml) and N,N-dimethylbenzylamine (two drops), in dry tetrahydrofuran (20 ml). After twenty minutes the crude amine (9) in dry tetrahydrofuran (10 ml) and methylene dichloride (10 ml) was added dropwise over ten minutes to the mixed anhydride at −10° C. After a further twenty minutes the reaction mixture was filtered, the filtrate concentrated and the residue taken up in ethyl acetate and washed successively with dilute HCl, dilute NaHCO$_3$ solution, brine, dried (MgSO$_4$) and evaporated. Chromatography of the residue on silica H afforded the product (23) (2.65 g) as a white amorphous solid. [α]$_D^{18.5}$ −21.7° (c 2.7 in CHCl$_3$); ν$_{max}$. (CHCl$_3$) 3420, 3315, 1775, 1740, 1695 cm$^{-1}$ δ ppm (CDCl$_3$) 1.34, 1.36, 1.41 and 1.45 (together 3H, s), 1.70, 1.81, 2.37 and 2.44 (together 1H, d, J 2 Hz), 3.7–4.0 (4H, broad s), 4.4–4.6 (1H, m), 4.7–5.6 (7H, m), 6.2–6.5 (1H, m), 6.9–7.2 (1H, m, exchange), 7.2–7.6 (12H, m), 8.13 (2H, d, J 9 Hz). (Found: C, 61.9; H, 5.0; N, 8.4; C$_{34}$H$_{32}$N$_4$O$_{10}$ requires C, 62.2; H, 4.9; N, 8.5%).

(b)

(3RS,4SR)-(1-Benzyloxycarbonyl-2-hydroxyprop-1-enyl)-4-ethynyl-3-[N-(p-nitrobenzyloxycarbonyl)-D-α-phenylglycylamino]-azetidin-2-one (24)

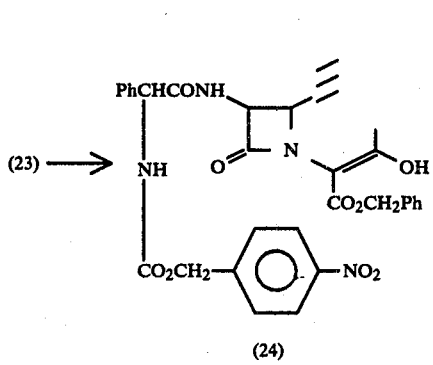

The ketal (23) (0.328 g) was transformed, using the procedure in Example 2(b), to the enol (24) (0.242 g) $[\alpha]_D^{18.5}$ −21.5° (c 2 in CHCl$_3$); $\nu_{max}$. (CHCl$_3$) 3415, 3300, 1770, 1730, 1690, 1660, 1620 cm$^{-1}$; δ ppm (CDCl$_3$) 1.84 and 2.34 (together 1H, d, J 2 Hz), 2.01 (together 3H, s), 4.4–4.6 (1H, m), 4.8–5.4 (6H, m), 6.15–6.40 (1H, m), 6.8–7.6 (13H, m), 8.14 (2H, d, J 9 Hz), 12.27 (1H, s, exchange). (Found: C, 62.5; H, 4.7; N, 9.0; $C_{32}H_{28}N_4O_9$ requires C, 62.7; H, 4.6; N, 9.1%).

(c)

(3RS,4SR)-1-(1-Benzyloxycarbonyl-2-mesyloxyprop-1-enyl)-4-ethynyl-3-[N-(p-nitrobenzyloxycarbonyl)-D-α-phenylglycylamino]-azetidin-2-one (25)

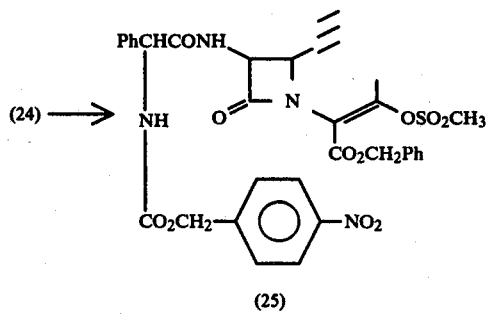

The β-lactam (24) (1 g) was transformed into the mesylate (25) (0.442 g) as described in Example 1(f). $\nu_{max}$. (CHCl$_3$) 3410, 3300, 1780, 1730, 1695, 1640, 1610 cm$^{-1}$; δ ppm (CDCl$_3$) 1.82 (1H, d, J 2 Hz), 2.52 and 2.54 (together 3H, s), 3.09 and 3.13 (together 3H, s), 4.65–4.90 (1H, m), 5.1–5.5 (5H, m), 6.1–6.4 (1H, m, exchange), 6.6–6.9 (1H, m, exchange), 7.1–7.6 (12H, m), 8.15 (2H, s, J 9 Hz). (Found: C, 57.7; H, 4.5; N, 8.1; S, 4.1; $C_{33}H_{30}N_4O_{11}S$ requires C, 57.4; H, 4.3; N, 8.1; S, 4.6%).

(d) (4bRS,5RS)-Benzyl 5,6-Dihydro-9-methyl-6-oxo-5-[N-(p-nitrobenzyloxycarbonyl)-D-α-phenylglycylamino]-4bH-azeto-[2,1-c]-v-triazolo-[1,5-a]pyrazine-8-carboxylate (27)

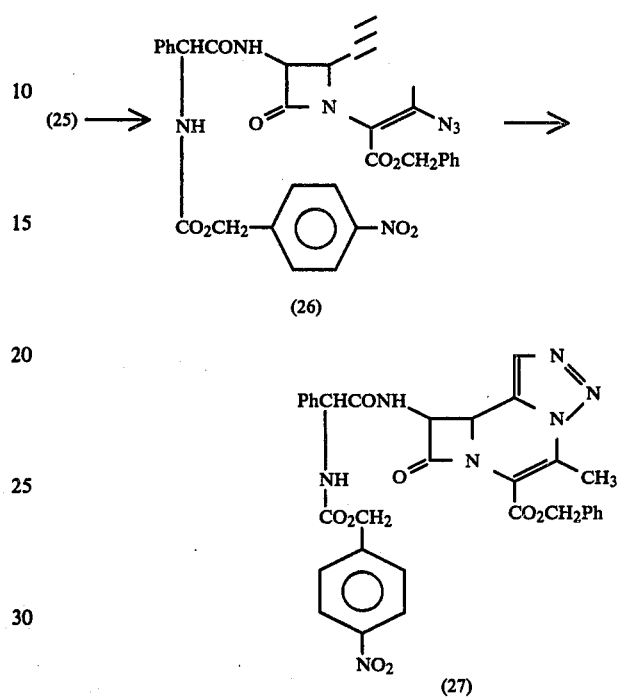

The mesylate (25) (141 mg) was converted to the β-lactam (27) (68 mg) via the azide (26) as described in Example 1(g). $[\alpha]_D^{20}$ −17.8° (c 0.9 in CHCl$_3$); $\lambda_{max}$. (EtOH) 277 n.m. (ε 15623); $\nu_{max}$. (Nujol) 3400, 3310, 1780, 1720, 1695, 1680, 1635 cm$^{-1}$; δ ppm (CDCl$_3$) 2.82 (3H, s), 4.9–5.4 (5H, m), 5.6–5.8 (1H, m), 5.8–6.0 (1H, m), 6.9–7.8 (14H, m, reduced to 12H, m on exchange), 8.05–8.15 (2H, m), (E.I. Mass spectra showed no M$^+$, but very strong peaks at m/e 369 and 268 resulting from β-lactam cleavage. Found: m/e 369.0961; $C_{18}H_{15}N_3O_6$ requires m/e 369.0961 and m/e 268.0963; $C_{14}H_{12}N_4O_2$ requires m/e 268.0960).

(e)

(4bRS,5RS)-5,6-Dihydro-9-methyl-6-oxo-5-D-α-phenylglycylamino-4bH-azeto-[2,1-c]-v-triazolo[1,5-a]pyrazine-8-carboxylic acid, p-toluidine salt (28)

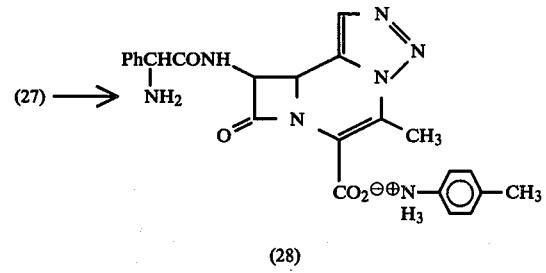

The ester (27) (35 mg) was dissolved in dioxan (15 ml) and water (3 ml) and hydrogenated using 10% palladium/carbon catalyst (18 mg). The mixture was filtered through Kieselguhr, and the filtrate evaporated to dryness, followed by re-evaporation from ethanol, then toluene to give a gum. Trituration with ether gave the p-toluidine salt (28); (24 mg) as a pale yellow solid $[\alpha]_D^{22}$ −11.25° (c 0.32 in DMSO); $\lambda_{max}$ (EtOH) 245 ($\epsilon$ 9140) 284 nm (5820); $\nu_{max}$ (KBr) 3400b, 1775, 1715, 1680, 1610 cm$^{-1}$.

EXAMPLE 4

(4bRS,5RS) 5-Acetamido-5,6-dihydro-9-methyl-6-oxo-4bH-azeto-[2,1-c]-v-triazolo-pyrazine-8-carboxylic acid (35)

(a)

(3RS,4SR)-3-Azido-1-(1-benzyloxycarbonyl-2-hydroxyprop-1-enyl)-4-ethynyl-azetidin-2-one (29)

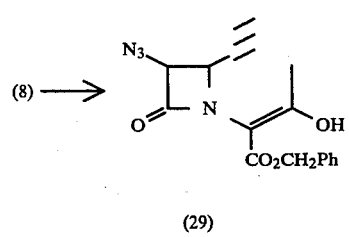

(29)

The azide (8) (0.369 g) was converted, as in Example 2(b), to the enol (29) (0.243 g), which was isolated as an oil. $\nu_{max}$ (CHCl$_3$) 3300, 2115, 1775, 1660, 1620 cm$^{-1}$; $\delta$ ppm (CDCl$_3$) 2.16 (3H, s), 2.58 (1H, d, J = 1 Hz), 4.57 (2H, s), 5.20 (2H, AA′), 7.33 (5H, s), 12.30 (1H, s, exchange). (Found: $\underline{M}^+$ 326.1029; C$_{16}$H$_{14}$N$_4$O$_4$ requires $\underline{M}$, 326,1015).

(b)

(3RS,4SR)-3-Azido-1-(1-benzyloxycarbonyl-2-mesyloxyprop-1-enyl)-4-ethynyl-azetidin-2-one (30)

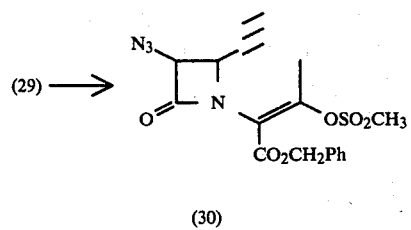

(30)

The enol (29) (214 mg) was transformed as in Example 1(f) to the mesylate (30) (202 mg) which was obtained as an oil. $\nu_{max}$ (CHCl$_3$) 3295, 2125, 1780, 1730, 1635 cm$^{-1}$; $\delta$ ppm (CDCl$_3$) 2.59 (1H, d, J = 2 Hz), 2.67 (3H, s), 3.22 (3H, s), 4.64 (1H, d, J 6 Jz), 4.80 (1H, dd, J 6 and 2 Hz), 5.22 (2H, AA′), 7.35 (5H, s). Inter alia peaks at $\delta$ 2.36 and $\delta$ 2.97 are assumed to belong to the minor Z-isomer. (Found: $\underline{M}$—N$_2$ + 376.0709; C$_{17}$H$_{16}$N$_2$O$_6$S requires $\underline{M}$—N$_2$, 376.0727).

(c) (4bRS,5RS) Benzyl 5-Azido-5,6-dihydro-9-methyl-6-oxo-4bH-azeto[2,1-c]-v-triazolo[1,5-a]-pyrazine-8-carboxylate (32)

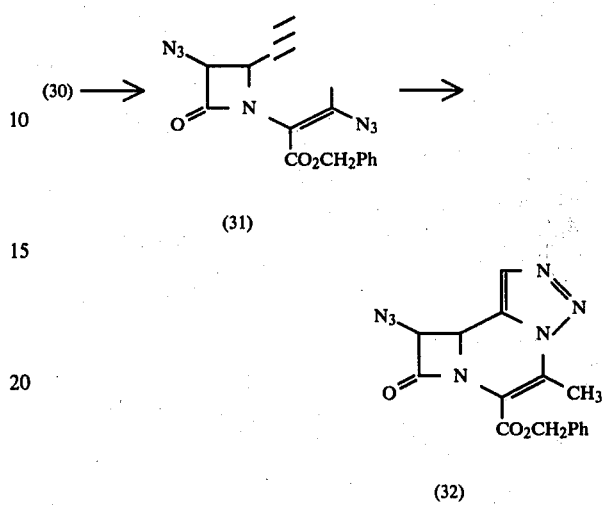

The mesylate (30) (163 mg) in dry dimethylformamide (1 ml) was vigorously stirred with finely powdered sodium azide (29 mg) at ambient temperature for ten minutes. The reaction mixture was poured into ethyl acetate, washed with water, very dilute HCl, brine, dried (MgSO$_4$) and evaporated to give (31) as an oil. $\nu_{max}$ (CHCl$_3$) 3300, 2125, 1780, 1725, 1620 sh. cm$^{-1}$.

The total crude product (31) was dissolved in benzene (20 ml) and gently refluxed for ten minutes, cooled and evaporated. Chromatography on silica H gave the product (32) (48 mg) as an amorphous solid. $\lambda_{max}$ (EtOH) 298 nm ($\epsilon$ 10648); $\nu_{max}$ (CHCl$_3$) 2125, 1795, 1725, 1630 cm$^{-1}$; $\delta$ ppm (CDCl$_3$) 2.92 (3H, s), 5.02 (1H, dd, J 4.92 and 1.83 Hz), 5.31 (2H, s), 5.34 (1H, d, J 4.92 Hz), 7.39 (5H, s), 7.65 (1H, d, J 1.83 Hz). (Found: $\underline{M}^+$ 351.1073; C$_{16}$H$_{13}$N$_7$O$_3$ requires $\underline{M}$, 351.1077).

(d) (4bRS,5RS) Benzyl 5-Acetamido-5,6-dihydro-9-methyl-6-oxo-4bH-azeto[2,1-c]-v-triazolo-[1,5-a]-pyrazine-8-carboxylate (34)

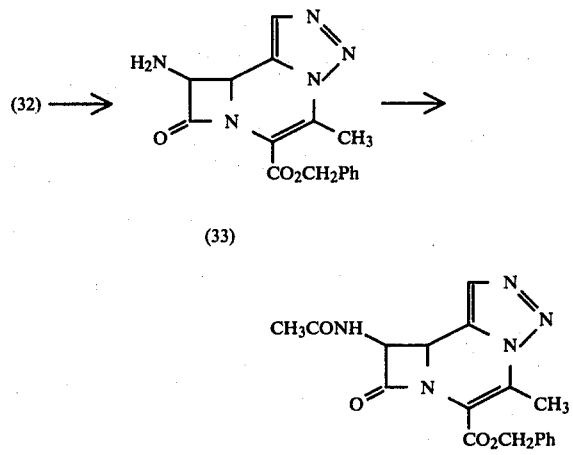

To the β-lactam (32) (45 mg) in dry methylene dichloride (3 ml) at 0° was added triethylamine (14 mg). Hydrogen sulphide was bubbled through the mixture for five minutes and the resulting pale yellow solution stood at 0° for twenty-five minutes. The solvent was then removed under reduced pressure and the residue re-evaporated (×3) from methylene dichloride to afford the crude amine (33) as a solid. Without further purification the β-lactam (33) was dissolved in dry methylene dichloride (3 ml) at −20° and triethylamine (14 mg) added, followed by dropwise addition of acetyl chloride (11 mg) in methylene dichloride (0.2 ml) over one minute. The reaction mixture was diluted with methylene dichloride, washed with brine, dried (MgSO₄) and evaporated to a gum. Chromatography on silica H afforded the product (34) (28 mg) as a white solid λ$_{max.}$ (EtOh) 301 n.m. (ε 9715); ν$_{max.}$ (CHCl₃) 3425, 1785, 1720, 1685, 1630 cm⁻¹; δ ppm (CD₃OD/(CD₃)₂CO) 1.94 (3H, s), 2.88 (3H, s), 5.2 (1H, d, J 5 Hz), 5.31 (2H, s), 5.67 (1H, d, J 5 Hz), 7.2–7.6 (6H, m), 7.53 (1H, s). (Found: $\underline{M}$⁺+H, 368.1378; C₁₈H₁₈N₅O₄ requires $\underline{M}$+H, 368.1357).

(e) (4bRS,5RS) 5-Acetamido-5,6-dihydro-9-methyl-6-oxo-4bH-azeto-[2,1-c]-v-triazolo-pyrazine-8-carboxylic acid (35)

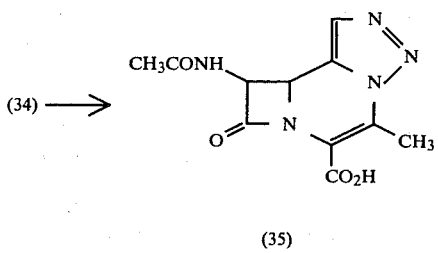

(35)

The ester (34) (28 mg) was hydrogenated as described in Example 1(h) to provide the free acid (35) (19 mg) as a white amorphous solid. λ$_{max.}$ (EtOH) 287 n.m. (ε6925); νmax. (KBr) 3400b, 1780, 1670, 1630 cm⁻¹.

EXAMPLE 5

(4bR,5R) 5,6-Dihydro-5-D-α-hydroxyphenylacetamido-9-methyl-6-oxo-4bH-azeto-[2,1-c]-v-triazolo-[1,5-a]-pyrazine-8-carboxylic acid (39)

(a) (4bR,5R)-Benzyl 5,6-Dihydro-5-D-α-hydroxyphenylacetamido-9-methyl-6-oxo-4bH-azeto-[2,1-c]-v-triazolo-[1,5-a]-pyrazine-8-carboxylate (36), (4bS,5S)-Benzyl-triazolo-[1,5-a]-pyrazine-8-carboxylate (37) and (4bS,5S)-Benzyl 5-Amino-5,6-dihydro-9-methyl-6-oxo-4bH-azeto-[2,1-c]-v-triazolo-[1,5-a]-pyrazine-8-carboxylate (38)

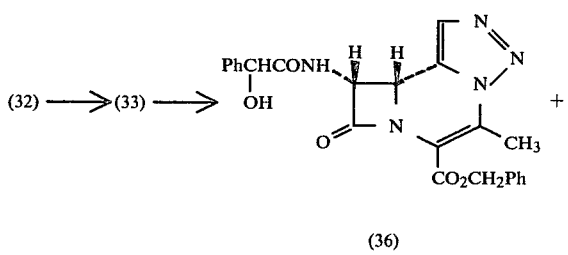

(36)

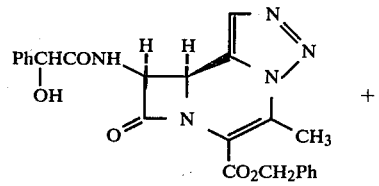

(37)

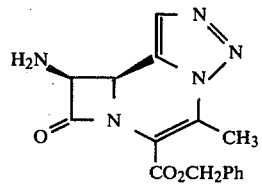

(38)

The β-lactam (33; prepared from (32) as described in Example 4(d) (75 mg) in dry methylene dichloride at −20° was stirred with D-Mandelyl-O-carboxyanhydride (42 mg) for one hour. The reaction mixture was diluted with methylene dichloride, carefully washed with dilute NaHCO₃ solution, brine, dried (MgSO₄) and evaporated. Chromatography on silica H afforded the product (36) (29 ng) as a white solid. [α]$_D^{22}$−21.6° (c 2.9 in CHCl₃); λ$_{max.}$ (EtOH) 301 n.m. (ε9450); ν$_{max.}$ (CHCl₃) 3400b, 1790, 1725, 1690, 1630 cm⁻¹; δ ppm (CDCl₃) 2.87 (3H, s), 4.0–4.3 (1H, broad s, exchange), 4.94 (1H, d, 5 Hz), 5.10 (1H, s), 5.29 (2H, s), 5.69 (1H, dd, J 8 and 5 Hz), 6.91 (1H, s), 7.34 (10H, s), 7.60 (1H, d, J 8 Hz). (Found: $\underline{M}$ —H₂O⁺, 441.1445; C₂₄H₁₉N₅O₄ requires $\underline{M}$—H₂O, 441.1433. C.I. mass spectra show M+H at 460).

Further elution of the column provided the diastereoisomer (37) (12 mg) as a white solid [α]$_D^{22}$−22.2° (c 1.2 in CHCl₃); λ$_{max.}$ (EtOH) 302 n.m. (ε8010); ν$_{max.}$ (CHCl₃) 3400b, 1790, 1725, 1690, 1630 cm⁻¹; δ ppm (CDCl₃) 2.79 (3H, s), 4.1–4.5 (1H, broad s, exchange) 4.94 (1H, d, J 5 Hz), 5.06 (1H, s), 5.26 (2H, s), 5.68 (1H, dd, J 8 and 5 Hz), 6.91 (1H, s), 7.34 (11H, m, collapses to 10H on exchange). (Found: $\underline{M}$⁺ 459.1544; C₂₄H₂₁N₅O₅ requires $\underline{M}$, 459.1540).

The third product eluted from the column was the amine (38) (25mg) as a white solid [α]$_D^{22}$−52.97° (c 1.5 in CHCl₃); λ$_{max.}$ (EtOH) 300 n.m. (ε7905); ν$_{max.}$ (Nujol) 3380, 1770, 1718, 1630 cm⁻¹; δ ppm [(CD₃)₂CO] 2.87 (3H, s), 5.24 (1H, d, J 5 Hz), 5.32 (2H, s), 5.7 (1H, d, J 5 Hz), 7.3–7.6 (5H, m), 7.57 (1H, s). (Found: $\underline{M}$⁺, 325.1169; C₁₆H₁₅N₅O₃ requires M, 325.1173).

(b) (4bR,5R)
5,6-Dihydro-5-D-α-hydroxyphenylacetamido-9-methyl-6-oxo-4bH-azeto-[2,1-c]-v-triazolo-[1,5-a]-pyrazine-8-carboxylic acid (39)

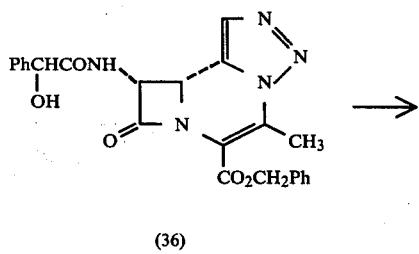

(36)

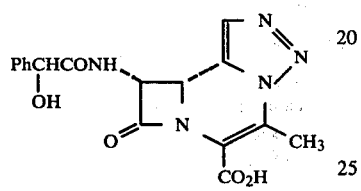

(39)

The ester (36) (23 mg) was hydrogenated as described in Example 1(h) to provide the free acid (39) (13 mg) as a white solid. λ$_{max}$. (EtOH) 290 n.m. (ε6490); ν$_{max}$. (KBr) 3400, 1750, 1675, 1640 cm$^{-1}$.

EXAMPLE 6

(4bS,5S)-5,6-Dihydro-5-D-α-hydroxyphenylacetamido-9-methyl-6-oxo-4bH-azeto-[2,1-c]-v-triazolo-[1,5-a]-pyrazine-8-carboxylic acid (40)

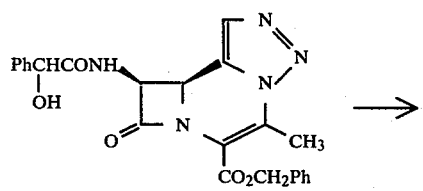

(37)

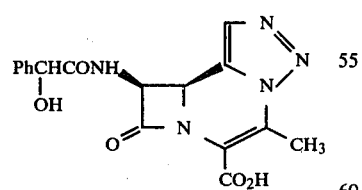

(40)

The ester (37) (15 mg) was hydrogenated as described in Example 1(h) to provide the free acid (40) (10 mg) as a white solid. λ$_{max}$. (EtOH) 287 n.m. (4792); ν$_{max}$. (KBr) 3400, 1765, 1670, 1640 cm$^{-1}$.

EXAMPLE 7

(4bS,5S)-5,6-Dihydro-9-methyl-6-oxo-5-phenoxyacetamido-4bH-azeto-[2,1-c]-v-triazolo-[1,5-a]-pyrazine-8-carboxylic acid (42)

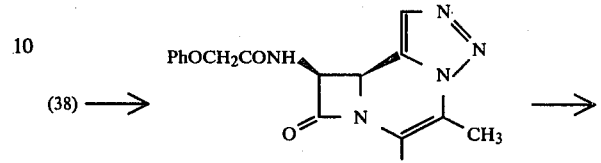

(41)

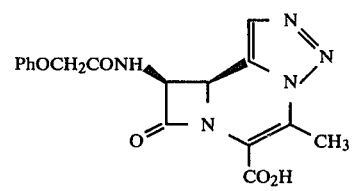

(42)

The amine (38) (14 mg) was acylated with phenoxyacetyl chloride, as described in Example 4(d), to give the acylamino derivative (41) (20 mg) as an amorphous solid. (Identical physical data to (14): Example 1(g). [α]$_D^{22}$−5.15° (c 3.25 in CHCl$_3$). The ester (41) (20 mg) was hydrogenated as described in Example 1(h) to give the free acid (42) (10 mg) as a white solid. (Identical physical data to (15); Example 1(n) [α]$_D^{22}$−21.1° (c 1.2 in DMSO).

EXAMPLE 8

(4bRS,5RS)5,6-Dihydro-9-methyl-6-oxo-5-(2-thienylacetamido)-4bH-azeto-[2,1-c]-v-triazolo-[1,5-a]-pyrazine-8-carboxylic acid, p-toluidine salt (55)

(a) Ethyl α-(3-Trimethylsilylpropynylidene amino)acetoacetate ethylene ketal (44)

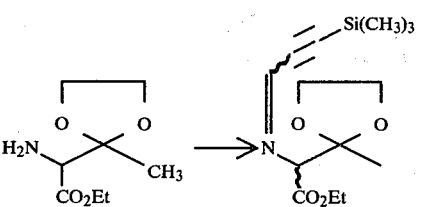

Ethyl α-aminoacetoacetate ethylene ketal (43: T. W. Doyle et al, Canad, J. Chem. 1977, 55, 484 (14.8 g) was reacted with trimethylsilylprop-2-yn-1-al (9.0 g) and anhydrous magnesium sulphate (5 g) as described in Example 1 to give the Schiff base (44) (21 g) as an orange gum. ν$_{max}$. (CHCl$_3$) 1730, 1610 cm$^{-1}$.

(b)

(3RS,4RS)-3-Azido-1-(1-ethoxycarbonyl-2,2-ethyleneketalpropyl)-4-trimethylsilylethynyl-azetidin-2-one (45) and (3RS,4SR)-3-Azido-1-(1-ethoxycarbonyl-2,2-ethyleneketalpropyl)-4-trimethylsilylethynyl-azetidin-2-one (46)

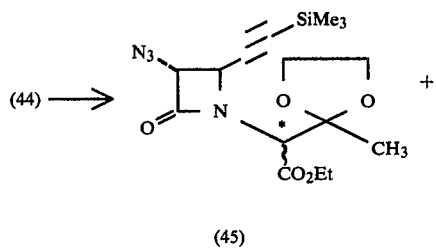

(45)

(46)

The Schiff base (44) (21 g) was converted as described in Exaple 1(b) to the β-lactam (45; mixture of isomers * ≈ 4:1) (5.06 g) $\nu_{max}$. (CHCl$_3$) 2120, 1775, 1740 cm$^{-1}$; δ ppm (CDCl$_3$) 0.18 (9H, t, J 7 Hz), 1.42 (0.6H, s), 1.54 (2.4H, s), 3.99 (4H, s), 4.24 (0.4H, q, J 7 Hz), 4.28 (1.6H, q, J 7 Hz), 4.3 (0.8H, s), 4.47 (1H, d, J 2 Hz), 4.5 (0.2H, s), 4.57 (1H, d, J 2 Hz). (Found: C, 50.3; H, 6.1; N, 14.4; C$_{16}$H$_{24}$N$_4$O$_5$Si requires C, 50.5; H, 6.3; N, 14.7%), and β-lactam (46; mixture of isomers * ≈ 3.2) (3.32 g) $\nu_{max}$. (CHCl$_3$) 2115, 1770, 1740 cm$^{-1}$; δ ppm (CDCl$_3$) 0.18 (9H, s), 1.28 (1.2H, t, J 7 Hz), 1.30 (1.8H, t, J 7 Hz), 1.46 (1.2H, s), 1.54 (1.8H, s), 3.98 (4H, s), 4.22 (2H, q, J 7 Hz), 4.44 (0.6H, s), 4.48 (0.4H, s), 4.51 (1H, d, J 5 Hz), 4.75 (0.4H, d, J 5 Hz), 4.97 (0.6H, d, J 5 Hz). (Found: C, 50.2; H, 6.2; N, 15.0; C$_{16}$H$_{24}$N$_4$O$_5$Si requires C, 50.5; H, 6.3; N, 14.7%).

(c)

(3RS,4SR)-3-Azido-4-ethynyl-1-(1-p-nitrobenzyloxycarbonyl-2,2-ethyleneketalpropyl)-azetidin-2-one (48)

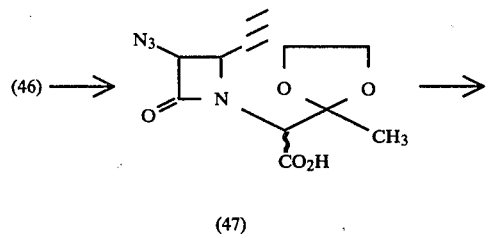

(47)

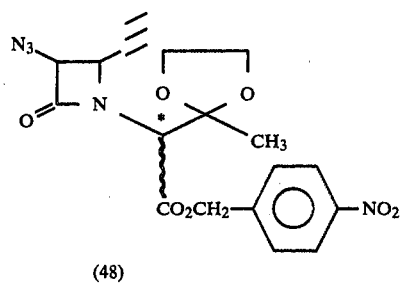

(48)

Dilute sodium hydroxide (38 ml. 0.25 N) was added dropwise, with cooling, over ten minutes to the ethyl ester (46) (1.64 g) in tetrahydrofuran (30 ml). After one hour at room temperature, the solution was carefully acidified to pH 3 with concentrated hydrochloric acid, saturated with salt and the upper organic layer separated. The aqueous layer was extracted with methylene dichloride (×3), and the combined organic extracts, washed with brine, dried (Na$_2$SO$_4$), evaporated, dried in vacuo to give the acid (47) (1.35 g), $\nu_{max}$. (CHCl$_3$) 3320, 2120, 1775, 1740 cm$^{-1}$. Without further purification, the crude acid (47) was dissolved in dry dimethylformamide (20 ml) containing p-nitrobenzyl bromide (1.03 g) and vigorously stirred with finely powdered anhydrous potassium carbonate (0.656 g) for seventeen hours. The reaction mixture was diluted with ethyl acetate, washed with dilute hydrochloric acid, brine, dried (MgSO$_4$) and evaporated. Chromatography on silica H afforded the required ester (48) (0.96 g) as a mixture of isomers. Ether trituration provided a pure sample of one isomer, m.p. 85°-87° (ethyl acetate-light petroleum); $\nu_{max}$. (Nujol) 3250, 2110, 1765, 1735 cm$^{-1}$; δ ppm (CDCl$_3$) 1.53 (3H, s), 2.66 (1H, d, J ≈ 2 Hz), 3.93 (4H, s), 4.43 (1H, s), 4.64 (1H, d, J 5 Hz), 4.92 (1H, dd, J 5 and ≈ 2 Hz), 5.28 (2H, s), 7.51 (2H, d, J 9 Hz), 8.20 (2H, d, J 9 Hz). The ether-soluble material was a mixture of isomers (*) (≈ 2:1), $\nu_{max}$. (CHCl$_3$) 3310, 2125, 1780, 1760 cm$^{-1}$; δ ppm (CDCl$_3$) 1.44 (1H, s), 1.53 (2H, s), 2.55 (0.33H, d, J ≈ 2 Hz), 2.66 (0.67H d, J ≈ 2 Hz), 3.93 (4H, s), 4.43 (0.67H, s), 4.60 (0.33H, s), 4.64 (0.67H, J 5 Hz), 4.79 (0.33H, J 5 Hz), 4.91 (1H, dd, J 5 and ≈ 2 Hz), 5.28 (2H, s), 7.51 (2H, d, J 9 Hz), 8.20 (2H, d, J 9 Hz). (Found: C, 51.8; H, 4.0; N, 16.5; C$_{18}$H$_{17}$N$_5$O$_7$ requires C, 52.0; H, 4.1; N, 16.9%).

(d)

(3RS,4SR)-3-Azido-4-ethynyl-1-(1-p-nitrobenzyloxycarbonyl-2-hydroxyprop-1-enyl)-azetidin-2-one (49)

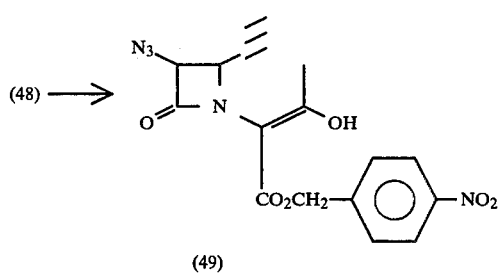

(49)

The azide (48) (0.9 g) was converted, as in Example 2(b), to the enol (49; 0.4 g) which was obtained as a white crystalline solid, m.p. 104°-105° (ethyl acetate-light petroleum); $\nu_{max}$. (Nujol) 3260, 2120, 1770, 1650, 1625 cm$^{-1}$; δ ppm (CDCl$_3$) 2.17 (3H, s), 2.62 (1H, d, J 2 Hz), 4.54–4.72 (2H, m), 5.3 (2H, s), 7.46 (2H, d, J 8 Hz), 8.21 (2H, d, J 8 Hz), 12.22 (1H, s, exchange). (Found: M$^+$, 371.0889; C$_{16}$H$_{13}$N$_5$O$_6$ requires M, 371.0863).

(e) (3RS,4SR)-3-Azido-4-ethynyl-1-(1-p-nitrobenzyloxycarbonyl-2-mesyloxyprop-2-enyl)-azetidin-2-one (50)

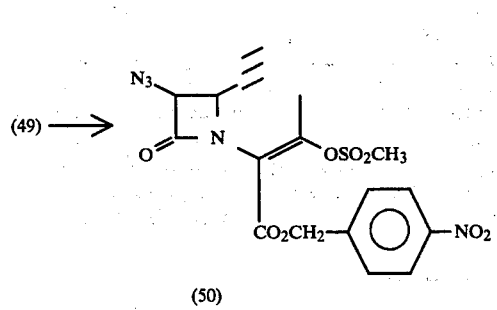

The enol (49) (0.36 g) was converted as described in Example 1(f) to the mesylate (50) (0.28 g) which was obtained as an unstable gum, ν$_{max}$. (CHCl$_3$) 3300, 2120, 1780, 1740, 1640, 1610 cm$^{-1}$; δ ppm (CDCl$_3$) 2.64 (3H, s, overlapping 1H, d, —C≡C—H), 3.24 (3H, s), 4.5–5.0 (2H, m), 5.30 (2H, AA'), 7.51 (2H, d, J 9 Hz), 8.20 (2H, d, J 9 Hz). Inter alia peaks at δ 2.37 and δ 3.17 are assigned to the minor Z-isomer. (Found: M—N$_2$$^+$ 421.0548; C$_{17}$H$_{15}$N$_3$O$_8$S requires M—N$_2$, 421.0619; C. I. spectra showed a strong M+NH$_4$$^+$ at 467).

(f) (4bRS,5RS) p-Nitrobenzyl 5-Azido-5,6-dihydro-9-methyl-6-oxo-4bH-azeto-[2,1-c]-v-triazolo-[1,5-a]-pyrazine-8-carboxylate (52)

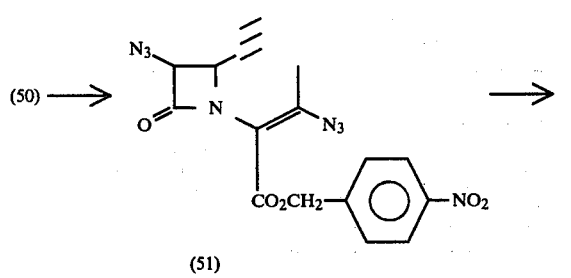

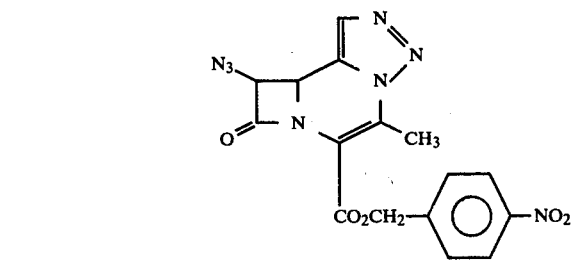

The mesylate (50) (0.28 g) was converted, as described in Example 4(c), to the azide (51) ν$_{max}$. (CHCl$_3$) 3300, 2120, 1775, 1730, 1610 cm$^{-1}$, and subsequently to the β-lactam (52: 0.07 g) which was isolated as an amorphous solid. λ$_{max}$. (EtOH) 267 (ε13745) 291 n.m. (13410); ν$_{max}$. (CHCl$_3$) 2115, 1790, 1730, 1630, 1610 cm$^{-1}$; δ ppm (CDCl$_3$) 2.97 (3H, s), 5.11 (1H, d, J 5 Hz), 5.26 and 6.12 (2H, ABq, J 14 Hz), 5.40 (1H, d, J 5 Hz), 7.5–7.8 (3H, m), 8.20 (2H, d, J 9 Hz). (Found: M$^+$ 396.0925, C$_{16}$H$_{12}$N$_8$O$_5$ requires M, 396,0930.

(g) (4bRS,5RS) p-Nitrobenzyl 5,6-Dihydro-9-methyl-6-oxo-5-(2-thienylacetamido)-4bH-azeto-[2,1-c]-v-triazolo-[1,5-a]-pyrazine-8-carboxylate (54)

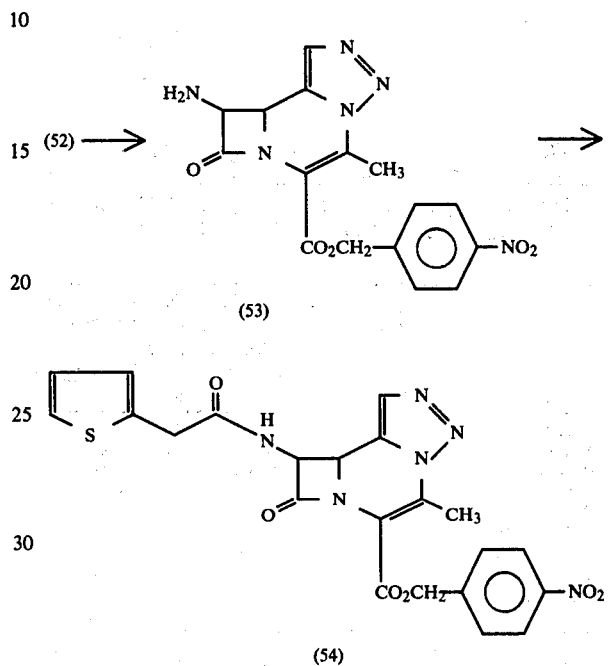

The azide (52) (0.027 g) was reduced to the amine (53) and then acylated with 2-thienylacetyl chloride (as described in Example 4(d) for the analogous benzyl ester) to give the acylamino derivative (54) (0.012 g), as a white solid, λ$_{max}$. (EtOH) 265 (ε14408) 291 n.m. (12349); ν$_{max}$. (Nujol) 1798, 1715, 1660, 1630 cm$^{-1}$; δ ppm ([CD$_3$]$_2$SO) 2.83 (3H, s), 3.63 and 3.72 (2H, ABq, J 15.5 Hz), 5.26 (1H, d, J 5.7 Hz), 5.42 and 5.55 (2H, ABq, J 14 Hz), 5.72 (1H, dd, J 5.1 and 8.3 Hz; collapses to d, J 5.1 Hz on exchange), 6.87 (1H, indistinct dd, J 3.2 Hz), 6.96 (1H, dd, J 5.1 and 3.2 Hz), 7.39 (1H, dd, J 5.1 and 1.2 Hz), 7.45 (1H, d, J 1.2 Hz), 7.75 (1H, d, J 8.9 Hz), 8.25 (1H, d, J 8.9 Hz), 8.87 (1H, d, J 8.3 Hz), exchange). (E.I. Mass spectra showed no M$^+$, but produced strong peaks at m/e 314 and 181 due to cleavage of the β-lactam ring. Found: m/e 314.0883, C$_{14}$H$_{12}$N$_5$O$_4$ requires m/e, 314.0887 and m/e 181.0220, C$_8$H$_7$NO$_2$S requires m/e 181.0198).

(h) (4bRS,5RS) 5,6-Dihydro-9-methyl-6-oxo-5-(2-thienylacetamido)-4bH-azeto-[2,1-c]-v-triazolo-[1,5-a]-pyrazine-8-carboxylic acid, p-toluidine salt) (55)

(54) →

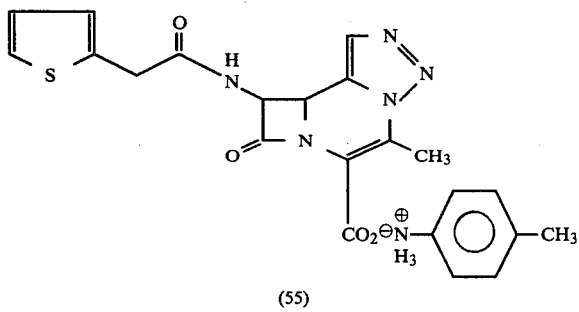

(55)

The ester (54) (0.01 g) was hydrogenated as described in Example 3(e) to provide the p-toluidine salt (55) (0.008 g) as a pale yellow solid. $\lambda_{max}$. (EtOH) 286 n.m. ($\epsilon$7780); $\nu_{max}$. (KBr) 3400 br, 1770, 1670, 1610 cm$^{-1}$.

wherein n is 0, 1 or 2; m is 0, 1 or 2; $A_1$ is alkyl of 1 to 6 carbon atoms, cycloalkyl of 3 to 6 carbon atoms, cyclohexenyl, cyclohexadienyl, phenyl, hydroxy-phenyl, thienyl or pyridyl; X is hydrogen, halo, carboxy, a pharmaceutically acceptable carboxyl ester moiety, azido, tetrazolyl, hydroxy, acyloxy, amino, ureido, guanidino or acylureido; $A_2$ is phenyl, 2,6-dimethoxyphenyl, 2-alkoxy-1-naphthyl, 3-phenylisoxazolyl or 3-phenyl-5-methylisoxazolyl; $X_1$ is $CH_2OCH_2$, $CH_2SCH_2$ or $(CH_2)_n$ wherein n is as above defined; and $X_2$ is an oxygen or sulphur atom; $R^2$ is hydrogen or alkyl of 1 to 4 carbon atoms; $R^3$ is hydrogen, alkyl of 1 to 4 carbon atoms unsubstituted or mono-substituted by carboxy, a pharmaceutically acceptable carboxyl ester moiety, hydroxy, alkyloxy of 1 to 4 carbon atoms, acyloxy or heterocyclylthio of the formula —S—Het wherein Het is diazolyl, triazolyl, tetrazolyl, thiazolyl, thiadiazolyl, thiatriazolyl, oxazolyl or oxadiazolyl un-

| | Antibacterial activity of 5-Acylamino-5,6-dihydro-9-methyl-6-oxo-4bH—azeto-[2,1-c]-v-triazolo-[1,5-a]-pyrazine-8-carboxylates | | | | | | | |
|---|---|---|---|---|---|---|---|---|
| | Minimum Inhibitory Concentration μg/ml[a] | | | | | | | |
| Organism | (15) | (22) | (28) | (35) | (39) | (40) | (42) | (55) |
| E. coli | >100 | 100 | >100 | >100 | >100 | >100 | >50 | — |
| K. aerogenes | >100 | >100 | >100 | >100 | >100 | 100 | >50 | 100 |
| P. mirabilis | >100 | 100 | >100 | >100 | >100 | 10 | >50 | 10 |
| S. typhimurium | >100 | 50 | >100 | 100 | >100 | 25 | >50 | — |
| B. subtilis | 5.0 | 100 | 10 | 5.0 | 100 | 0.5 | 0.5 | 0.5 |
| S. aureus Oxford | 25 | >100 | 100 | 100 | >100 | 25 | — | 10 |
| S. aureus Russell[b] | 100 | >100 | >100 | >100 | >100 | 100 | >50 | 100 |
| S. faecalis | >100 | >100 | >100 | >100 | >100 | 100 | 50 | 25 |
| S. pneumoniae | 2.5 | — | 10 | 5.0 | >100 | ≦0.2 | 5.0 | 2.5 |
| S. pyogenes | 5.0 | — | 2.5 | 2.5 | >100 | 50 | 2.5 | 0.2 |

[a]Determined by serial dilution on DST agar containing 10% horse blood using an inoculum of 0.001 ml of a 10$^{-2}$ dilution for Gram-positive bacteria or a 10$^{-4}$ dilution for Gram-negative organisms. MIC values were read after incubation at 37° for eighteen hours.
[b]β-lactamase-producing benzylpenicillin-resistant strain.

We claim:
1. A compound of the formula (I):

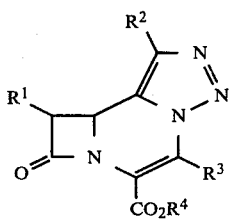

(I)

a pharmaceutically acceptable salt thereof or a pharmaceutically acceptable in-vivo hydrolyzable ester thereof wherein $R^1$ is amino, azido or a moiety of the formula $R^5$—CO—NH wherein $R^5$ is of the sub-formulae (a)-(d):

$A_1$—(CH$_2$)$_n$—CH—(CH$_2$)$_m$—CO   (a)
               |
               X $A_2$—CO   (b)

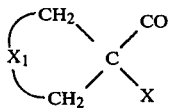   (c)

$A_2$—$X_2$—(CH$_2$)$_n$—CO   (d)

substituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo; and $R^4$ is hydrogen.

2. A compound according to claim 1 of the formula (II):

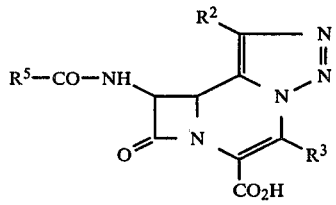

a pharmaceutically acceptable salt thereof or a pharmaceutically acceptable in-vivo hydrolyzable ester thereof wherein $R^2$ is hydrogen or alkyl of 1 to 4 carbon atoms; $R^3$ is hydrogen, alkyl of 1 to 4 carbon atoms unsubstituted or mono-substituted by carboxy, a pharmaceutically acceptable carboxyl moiety, hydroxy, alkyloxy of 1 to 4 carbon atoms, acyloxy or heterocyclylthio of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo; and $R^5$ is of the sub-formulae (a)-(d):

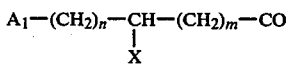  (a)

  (b)

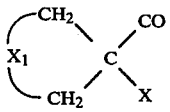  (c)

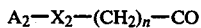  (d)

wherein n is 0, 1 or 2; m is 0, 1 or 2; $A_1$ is alkyl of 1 to 6 carbon atoms, cycloalkyl of 3 to 6 carbon atoms, cyclohexenyl, cyclohexadienyl, phenyl, hydroxy-phenyl, thienyl or pyridyl; X is hydrogen, halo, carboxy, a pharmaceutically acceptable carboxy ester moiety, azido, tetrazolyl, hydroxy, acyloxy, amino, ureido, guanidino or acylureido; $A_2$ is phenyl, 2,6-dimethoxyphenyl, 2-alkoxy-1-naphthyl, 3-phenylisoxazolyl or 3-phenyl-5-methylisoxazolyl; $X_1$ is $CH_2OCH_2$, $CH_2OCH_2$, $CH_2SCH_2$ or $(CH_2)_n$ wherein n is as above defined; and $X_2$ is an oxygen or sulphur atom.

3. A compound according to claim 2 wherein $R^2$ is hydrogen.

4. A compound according to claim 2 wherein $R^3$ is hydrogen, methyl, ethyl, propyl, butyl, acetoxymethyl or heterocyclicthio methyl wherein the heterocyclylthio is of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo.

5. A compound according to claim 2 wherein $R^5$ is a group of the sub-formulae (e) or (f):

  (e)

or

  (f)

wherein $R^6$ is phenyl, thienyl or phenoxy; $R^7$ is hydrogen or methyl; $R^8$ is phenyl, p-hydroxyphenyl, thienyl or cyclohexadienyl; and $R^9$ is hydroxyl amino, carboxyl, lower alkyl, phenyl, tolyl or indanyl ester thereof.

6. A compound according to claim 2 wherein $R^5CO$ is a D-phenylglycyl, D-p-hydroxyphenylglycyl, D-mandelyl, malonyl, benzoyl, 2-thienylacetyl, 3-thienylacetyl, 2-thienyl-α-carboxyacetyl, 3-thienyl-α-carboxyacetyl or phenoxyacetyl.

7. A compound according to claim 2 wherein $R^1$ is amino or azido.

8. A pharmaceutical composition useful for treating bacterial infections in animals which comprises an antibacterially effective amount of a compound of the formula (I):

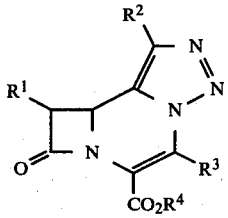  (I)

a pharmaceutically acceptable salt thereof or a pharmaceutically acceptable in-vivo hydrolyzable ester thereof wherein $R^1$ is amino, azido or a moiety of the formula $R^5$—CO—NH wherein $R^5$ is of the sub-formulae (a)-(d):

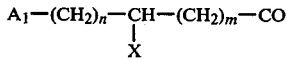  (a)

  (b)

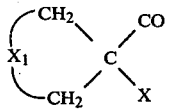  (c)

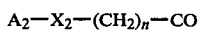  (d)

wherein n is 0, 1 or 2; m is 0, 1 or 2; $A_1$ is alkyl of 1 to 6 carbon atoms, cycloalkyl of 3 to 6 carbon atoms, cyclohexenyl, cyclohexadienyl, phenyl, hydroxy-phenyl, thienyl or pyridyl; X is hydrogen, halo, carboxy, a pharmaceutically acceptable carboxyl ester moiety, azido, tetrazolyl, hydroxy, acyloxy, amino, ureido, guanidino or acylureido; $A_2$ is phenyl, 2,6-dimethoxyphenyl, 2-alkoxy-1-naphthyl, 3-phenylisoxazolyl or 3-phenyl-5-methylisoxazolyl; $X_1$ is $CH_2OCH_2$, $CH_2SCH_2$ or $(CH_2)_n$ wherein n is as above defined; and $X_2$ is an oxygen or sulphur atom; $R^2$ is hydrogen or alkyl of 1 to 4 carbon atoms; $R^3$ is hydrogen, alkyl of 1 to 4 carbon atoms unsubstituted or mono-substituted by carboxy, a pharmaceutically acceptable carboxyl ester moiety, hydroxy, alkyloxy of 1 to 4 carbon atoms, acyloxy or heterocyclylthio of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo; and $R^4$ is hydrogen, in combination with a pharmaceutically acceptable carrier.

9. A composition according to claim 8 wherein the compound is of the formula (II):

a pharmaceutically acceptable salt thereof or a pharmaceutically acceptable in-vivo hydrolyzable ester thereof wherein $R^2$ is hydrogen or alkyl of 1 to 4 carbon atoms; $R^3$ is hydrogen, alkyl of 1 to 4 carbon atoms unsubstituted or mono-substituted by carboxy, a pharmaceutically acceptable carboxyl moiety, hydroxy, alkyloxy of 1 to 4 carbon atoms, acyloxy or heterocyclylthio of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo; and $R^5$ is of the sub-formulae (a)–(d):

$$A_1-(CH_2)_n-\underset{X}{CH}-(CH_2)_m-CO \quad (a)$$

$$A_2-CO \quad (b)$$

(c)

$$A_2-X_2-(CH_2)_n-CO \quad (d)$$

wherein n is 0, 1 or 2; m is 0, 1 or 2; $A_1$ is alkyl of 1 to 6 carbon atoms, cycloalkyl of 3 to 6 carbon atoms, cyclohexenyl, cyclohexadienyl, phenyl, hydroxy-phenyl, thienyl or pyridyl; X is hydrogen, halo, carboxy, a pharmaceutically acceptable carboxy ester moiety, azido, tetrazolyl, hydroxy, acyloxy, amino, ureido, guanidino or acylureido; $A_2$ is phenyl, 2,6-dimethoxyphenyl, 2-alkoxy-1-naphthyl, 3-phenylisoxazolyl or 3-phenyl-5-methylisoxazolyl; $X_1$ is $CH_2OCH_2$, $CH_2OCH_2$, $CH_2SCH_2$ or $(CH_2)_n$ wherein n is as above defined; and $X_2$ is an oxygen or sulphur atom.

10. A composition according to claim 9 wherein $R^2$ is hydrogen.

11. A composition according to claim 9 wherein $R^3$ is hydrogen, methyl, ethyl, propyl, butyl, acetoxymethyl or heterocyclycthio methyl wherein the heterocyclycthio is of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo.

12. A composition according to claim 9 wherein $R^5$ is a group of the sub-formulae (e) or (f):

$$R^6-\underset{R^7}{CH}- \quad (e)$$

or $$R^8-\underset{R^9}{CH}- \quad (f)$$

wherein $R^6$ is phenyl, thienyl or phenoxy; $R^7$ is hydrogen or methyl $R^8$ is phenyl, p-hydroxyphenyl, thienyl or cyclohexadienyl; and $R^9$ is hydroxyl amino, carboxyl, lower alkyl, phenyl, tolyl or indanyl ester thereof.

13. A composition according to claim 9 wherein $R^5CO$ is a D-phenylglycyl, D-p-hydroxyphenylglycyl, D-mandelyl, malonyl, benzoyl, 2-thienylacetyl, 3-thienylacetyl, 2-thienyl-α-carboxyacetyl, 3-thienyl-α-carboxyacetyl or phenoxyacetyl.

14. A composition according to claim 9 wherein $R^1$ is amino or azido.

15. A method of treating bacterial infections in humans and animals which comprises administering to a human or animal in need thereof an antibacterially effective amount of a compound of the formula (I):

(I)

a pharmaceutically acceptable salt thereof or a pharmaceutically acceptable in-vivo hydrolyzable ester thereof wherein $R^1$ is amino, azido or a moiety of the formula $R^5$—CO—NH wherein $R^5$ is of the sub-formulae (a)–(d):

$$A_1-(CH_2)_n-\underset{X}{CH}-(CH_2)_m-CO \quad (a)$$

$$A_2-CO \quad (b)$$

(c)

$$A_2-X_2-(CH_2)_n-CO \quad (d)$$

wherein n is 0, 1 or 2; m is 0, 1 or 2; $A_1$ is alkyl of 1 to 6 carbon atoms, cycloalkyl of 3 to 6 carbon atoms, cyclohexenyl, cyclohexadienyl, phenyl, hydroxy-phenyl, thienyl or pyridyl; X is hydrogen, halo, carboxy, a pharmaceutically acceptable carboxyl ester moiety, azido, tetrazolyl, hydroxy, acyloxy, amino, ureido, guanidino or acylureido; $A_2$ is phenyl, 2,6-dimethoxyphenyl, 2-alkoxy-1-naphthyl, 3-phenylisoxazolyl or 3-phenyl-5-methylisoxazolyl; $X_1$ is $CH_2OCH_2$, $CH_2SCH_2$ or $(CH_2)_n$ wherein n is as above defined; and $X_2$ is an oxygen or sulphur atom; $R^2$ is hydrogen or alkyl of 1 to 4 carbon atoms; $R^3$ is hydrogen, alkyl of 1 to 4 carbon atoms unsubstituted or mono-substituted by carboxy, a pharmaceutically acceptable carboxyl ester moiety, hydroxy, alkyloxy of 1 to 4 carbon atoms, acyloxy or heterocyclylthio of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo; and $R^4$ is hydrogen, in combination with a pharmaceutically acceptable carrier.

16. A method according to claim 15 wherein the compound is of the formula (II):

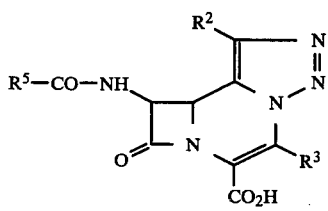

a pharmaceutically acceptable salt thereof or a pharmaceutically acceptable in-vivo hydrolyzable ester thereof wherein $R^2$ is hydrogen or alkyl of 1 to 4 carbon atoms; $R^3$ is hydrogen, alkyl of 1 to 4 carbon atoms unsubstituted or mono-substituted by carboxy, a pharmaceutically acceptable carboxyl moiety, hydroxy, alkyloxy of 1 to 4 carbon atoms, acyloxy or heterocyclylthio of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo; and $R^5$ is of the sub-formulae (a)–(d):

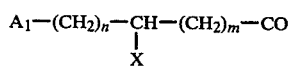 (a)

$A_2$—CO (b)

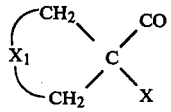 (c)

$A_2$—$X_2$—$(CH_2)_n$—CO (d)

wherein n is 0, 1 or 2; m is 0, 1 or 2; $A_1$ is alkyl of 1 to 6 carbon atoms, cycloalkyl of 3 to 6 carbon atoms, cyclohexenyl, cyclohexadienyl, phenyl, hydroxy-phenyl, thienyl or pyridyl; X is hydrogen, halo, carboxy, a pharmaceutically acceptable carboxy ester moiety, azido, tetrazolyl, hydroxy, acyloxy, amino, ureido, guanidino or acylureido; $A_2$ is phenyl, 2,6-dimethoxyphenyl, 2-alkoxy-1-naphthyl, 3-phenylisoxazolyl or 3-phenyl-5-methylisoxazolyl; $X_1$ is $CH_2OCH_2$, $CH_2OCH_2$, $CH_2SCH_2$ or $(CH_2)_n$ wherein n is as above defined; and $X_2$ is an oxygen or sulphur atom.

17. A method according to claim 16 wherein $R^2$ is hydrogen.

18. A method according to claim 16 wherein $R^3$ is hydrogen, methyl, ethyl, propyl, butyl, acetoxymethyl or heterocyclycthio methyl wherein the heterocyclycthio is of the formula —S—Het wherein Het is diazolyl, triazolyl, tetrazolyl, thiazolyl, thiadiazolyl, thiatriazolyl, oxazolyl or oxadiazolyl unsubstituted or substituted with one or two substituents selected from the group consisting of alkyl of 1 to 6 carbon atoms, alkoxy of 1 to 6 carbon atoms, hydroxyalkyl of 1 to 6 carbon atoms, alkenyl of 1 to 6 carbon atoms, alkoxyalkyl of 1 to 6 carbon atoms in each of the alkoxy and alkyl moieties, carboxyalkyl of 1 to 6 carbon atoms, alkylsulphonyl of 1 to 6 carbon atoms, carbamoyl, carbamoylmethyl, trifluoromethyl, hydroxy and halo.

19. A method according to claim 16 wherein $R^5$ is a group of the sub-formulae (e) or (f):

 (e)

or

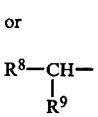 (f)

wherein $R^6$ is phenyl, thienyl or phenoxy; $R^7$ is hydrogen or methyl; $R^8$ is phenyl, p-hydroxyphenyl, thienyl or cyclohexadienyl; and $R^9$ is hydroxyl amino, carboxyl, lower alkyl, phenyl, tolyl or indanyl ester thereof.

20. A method according to claim 16 wherein $R^5CO$ is a D-phenylglycyl, D-p-hydroxyphenylglycyl, D-mandelyl, malonyl, benzoyl, 2-thienylacetyl, 3-thienylacetyl, 2-thienyl-α-carboxyacetyl, 3-thienyl-α-carboxyacetyl or phenoxyacetyl.

21. A method according to claim 16 wherein $R^1$ is amino or azido.

* * * * *